(12) United States Patent
Slatkine

(10) Patent No.: US 7,184,614 B2
(45) Date of Patent: Feb. 27, 2007

(54) METHOD AND APPARATUS FOR IMPROVING SAFETY DURING EXPOSURE TO A MONOCHROMATIC LIGHT SOURCE

(75) Inventor: Michael Slatkine, Herzlia (IL)

(73) Assignee: Inolase 2002 Ltd., Netanya (IL)

( * ) Notice: Subject to any disclaimer, the term of this patent is extended or adjusted under 35 U.S.C. 154(b) by 360 days.

(21) Appl. No.: 10/614,672

(22) Filed: Jul. 7, 2003

(65) Prior Publication Data
US 2004/0036975 A1    Feb. 26, 2004

(51) Int. Cl.
G02F 1/19 (2006.01)
G02B 5/02 (2006.01)

(52) U.S. Cl. .................. 385/5; 359/599; 359/600; 372/29.014

(58) Field of Classification Search ............ None
See application file for complete search history.

(56) References Cited

U.S. PATENT DOCUMENTS

| | | |
|---|---|---|
| 4,592,353 A | 6/1986 | Daikuzono |
| 4,736,743 A | 4/1988 | Daikuzono |
| 4,976,709 A | 12/1990 | Sand |
| 5,057,104 A | 10/1991 | Chess |
| 5,059,192 A | 10/1991 | Zaias |
| 5,066,293 A | 11/1991 | Furumoto |
| 5,217,455 A | 6/1993 | Tan |
| 5,226,907 A | 7/1993 | Tankovich |
| 5,282,797 A | 2/1994 | Chess |
| 5,312,395 A | 5/1994 | Tan et al. |
| 5,344,418 A | 9/1994 | Ghaffari |
| 5,401,270 A | 3/1995 | Muller et al. |
| 5,411,502 A | 5/1995 | Zair |
| 5,431,647 A | 7/1995 | Purcell, Jr. et al. |
| 5,449,354 A | 9/1995 | Konwitz et al. |

(Continued)

FOREIGN PATENT DOCUMENTS

EP    1116476    7/2001

(Continued)

OTHER PUBLICATIONS

International search report for PCT/IL02/00635, 6 pages, mailed Feb. 23, 2003.

(Continued)

*Primary Examiner*—John D. Lee
*Assistant Examiner*—Jerry T Rahll
(74) *Attorney, Agent, or Firm*—Roach Brown McCarthy & Gruber; Kevin D. McCarthy

(57) ABSTRACT

A method and apparatus are disclosed for improving bodily safety during exposure to an eye hazardous monochromatic treatment light source by diverging the light, such as with a diffusing unit attached to the light source distal end so that the radiance of the light exiting the distal end is an eye safe level. At a first position of the light source distal end substantially in contact with an outer surface of a target, the energy density of an exit beam from the distal end is suitable for effecting a desired treatment, and at a second non-contact position of the distal end the exit beam energy density is significantly less than a value suitable for effecting the treatment. In an additional embodiment, the diverging or diffusing unit has a device for evacuating vapors or particles from the target.

82 Claims, 22 Drawing Sheets

U.S. PATENT DOCUMENTS

| | | |
|---|---|---|
| 5,527,308 A | 6/1996 | Anderson et al. |
| 5,530,780 A | 6/1996 | Ohsawa |
| 5,558,660 A | 9/1996 | Dreier |
| 5,595,568 A | 1/1997 | Anderson et al. |
| 5,626,631 A | 5/1997 | Eckhouse |
| 5,630,811 A | 5/1997 | Miller |
| 5,655,547 A | 8/1997 | Karni |
| 5,735,844 A | 4/1998 | Anderson et al. |
| 5,745,519 A | 4/1998 | Ruda et al. |
| 5,814,041 A | 9/1998 | Anderson et al. |
| 5,853,407 A | 12/1998 | Miller |
| 5,871,521 A | 2/1999 | Kaneda et al. |
| 5,879,346 A | 3/1999 | Waldman et al. |
| 5,885,273 A | 3/1999 | Eckhouse et al. |
| 5,947,957 A | 9/1999 | Morris et al. |
| 5,961,475 A | 10/1999 | Guitay |
| 5,964,749 A | 10/1999 | Eckhouse et al. |
| 6,011,890 A | 1/2000 | Neuberger |
| 6,096,029 A | 8/2000 | O'Donnell, Jr. |
| 6,120,497 A | 9/2000 | Anderson et al. |
| 6,142,650 A | 11/2000 | Brown et al. |
| 6,165,170 A | 12/2000 | Wynne et al. |
| 6,197,020 B1 | 3/2001 | O'Donnell, Jr. |
| 6,214,034 B1 | 4/2001 | Azar |
| 6,261,310 B1 | 7/2001 | Neuberger et al. |
| 6,264,649 B1 | 7/2001 | Whitcroft et al. |
| 6,273,884 B1 | 8/2001 | Altshuler et al. |
| 6,280,438 B1 | 8/2001 | Eckhouse et al. |
| 6,530,920 B1 | 3/2003 | Whitcroft et al. |
| 2002/0034012 A1* | 3/2002 | Santoro et al. ............. 359/599 |
| 2002/0128635 A1 | 9/2002 | Altshuler et al. |
| 2004/0077977 A1 | 4/2004 | Ella et al. |
| 2004/0082940 A1 | 4/2004 | Black et al. |

FOREIGN PATENT DOCUMENTS

| | | |
|---|---|---|
| EP | 1168535 | 1/2002 |
| WO | WO 99/46005 A | 9/1999 |

OTHER PUBLICATIONS

Effects of Tissue Optical Clearing, . . . Lasers Light with Tissue (Vergas et al.) in Laser in Surgery and Medicine, Sep. 13, 2001, p. 26.

Effects of Tissue Optical Clearing, . . . , Lasers Light within Tissue (G. Vergas & A.J. Welch, "Laser in Surgery and Medicine", Supp. 13, 2001, p. 26).

PCT International Search Report for corresponding PCT application (PCT/IL02/00635) (6 pages).

PCT International Search Report for PCT application (PCT/IL03/00277) (3 pages).

* cited by examiner

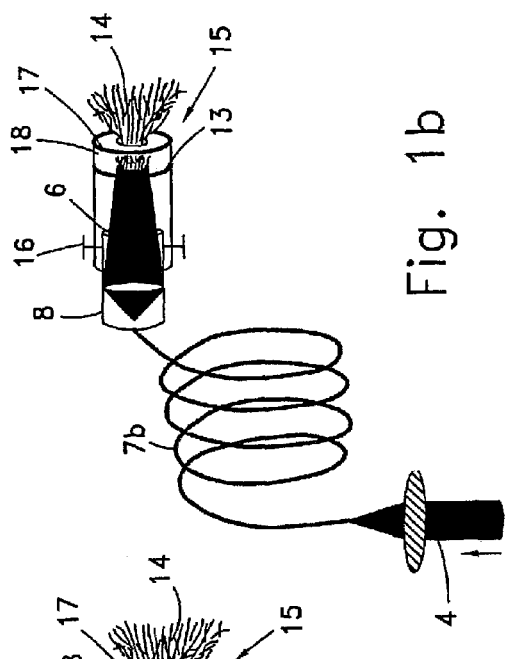
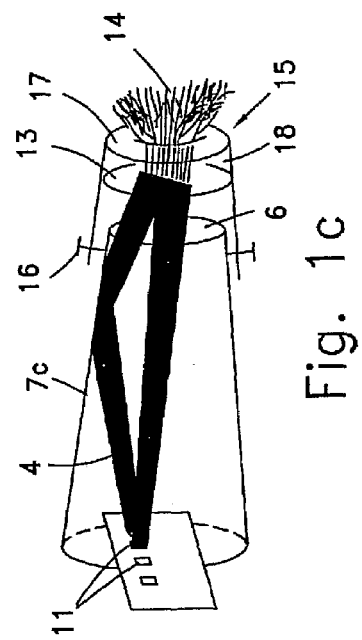
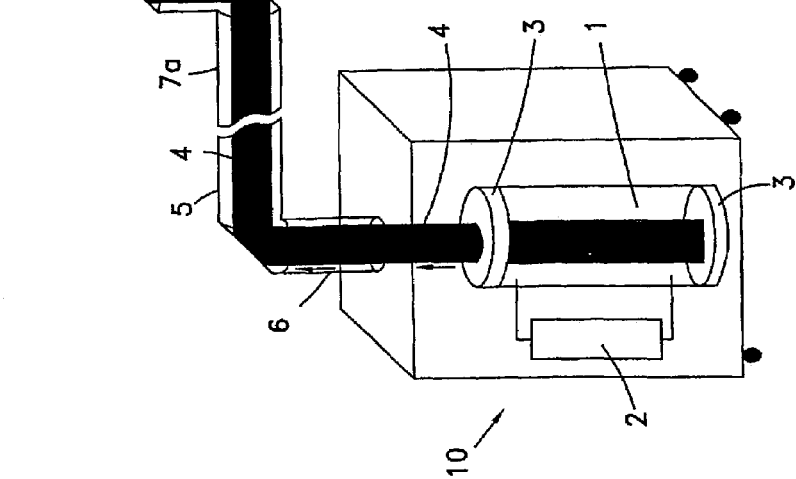

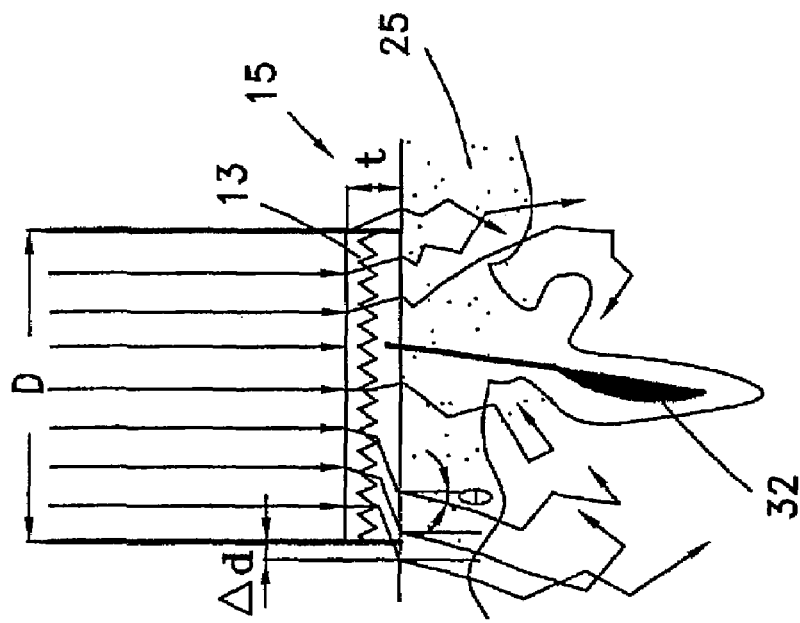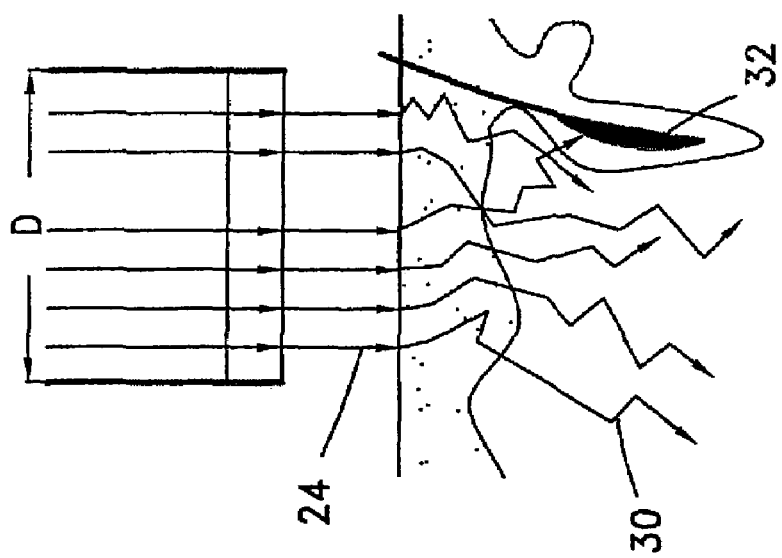
Fig. 5a
(PRIOR ART)
Fig. 5b

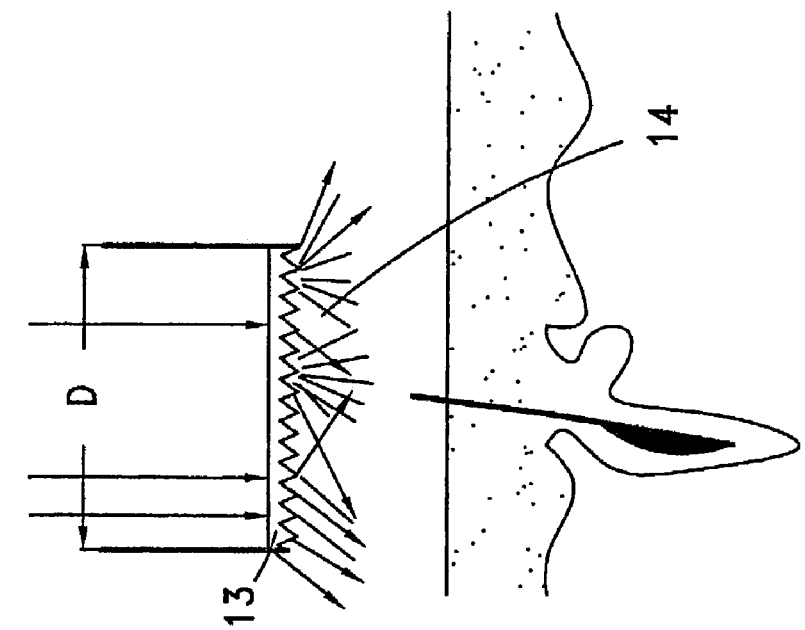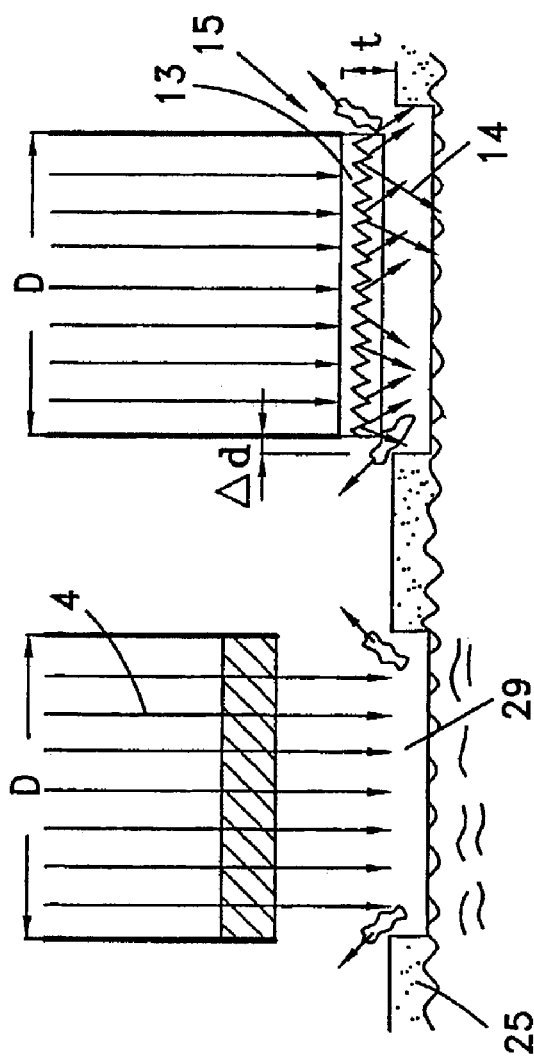
Fig. 5e
Fig. 5d
Fig. 5c (PRIOR ART)

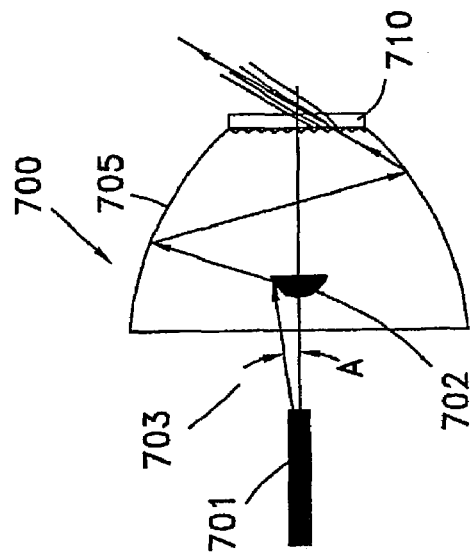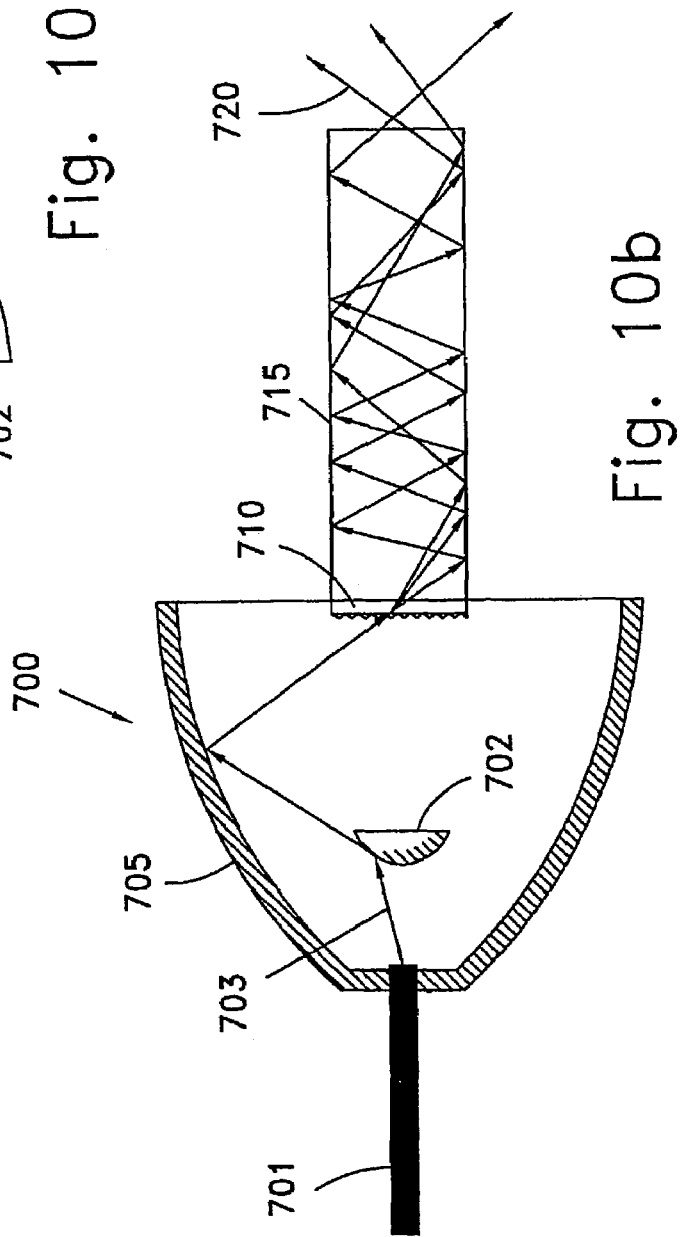
Fig. 10a
Fig. 10b

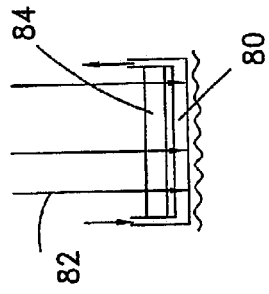
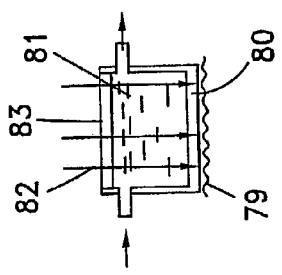
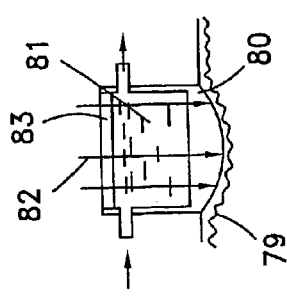
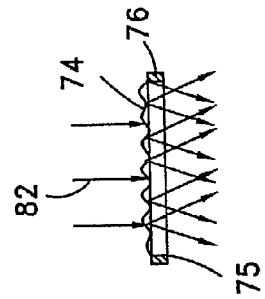
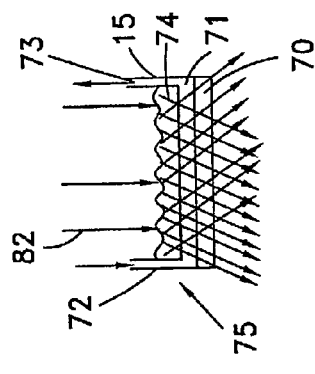
Fig. 15a (PRIOR ART)
Fig. 15b (PRIOR ART)
Fig. 15c (PRIOR ART)
Fig. 15d (PRIOR ART)
Fig. 15e
Fig. 15f

METHOD AND APPARATUS FOR IMPROVING SAFETY DURING EXPOSURE TO A MONOCHROMATIC LIGHT SOURCE

FIELD OF THE INVENTION

The present invention is related to the field of laser-based light sources. More particularly, the present invention is related to providing an eye-safe laser beam that is suitable for correcting aesthetic and medical skin disorders that require a very high energy density. Even more specifically, the present invention is related to a method and apparatus for improving bodily safety during exposure to a monochromatic light source by diverging the monochromatic light, such as with a highly durable diffuser, which provides the required energy density of light for desired applications at a very short distance but is inherently safe to the eyes of bystanders.

BACKGROUND OF THE INVENTION

Current medical and aesthetic laser systems are generally considered as high-risk systems due to the fact that the light beam that is emitted from these systems has only a low divergence, or even convergence. In these systems a light beam with a high energy density and high radiance, i.e. energy density per solid angle, is generated, which hardly attenuates as the beam propagates through air, or through an air-like medium, to a distant target whereat it could cause damage to bodily tissue. In the case of a laser source emitting visible, or near visible, light, damage could result by burning a small portion of an eye retina, if the beam is accidentally aimed at the eyes of a bystander. Such beam could even cause blindness.

Potential eye damage is further increased when using near infrared lasers which emit invisible radiation, since bystanders are unaware that a laser beam is being fired. Also, the extremely short pulse duration of a beam emitted by many laser systems does not allow enough time for one to react, such as by blinking or moving the eyes, as a result of the accidental firing of a laser beam.

Therefore, in order to minimize the risk of damaging living tissues, or causing other kind of damages, special, and often, high-cost precautions must be taken. For example, such precautions might include the use of expensive (and inconvenient to use) coated protective eyeglass filters with very high optical density and damage-resistant values to optical radiation (i.e. thermal and mechanical durability). Some of the properties of such filters are included in standard documents such as ANSI Z136.1, which is the basic American National Standard document regarding the safety of laser beams. A very similar basic document which sets safety labeling standards by the food and drug administration (FDA) is $1040.10 21 CFR Ch.1. Another document which sets manufacturing standards for the safety of eyes is ISO 15004:1997E. Other precautions forbid using highly reflective surfaces in a room, where the laser system is located. Special shades and/or curtains are also utilized for preventing an accidental laser beam from escaping the room or facility, thereby protecting people outside the treatment room.

Of all the risks, the risk of permanently blinding people is the most common and severe. The currently most eye-hazardous lasers are those referred to as a pulsed-laser. For example, a Ruby, Nd:YAG, Alexandrite, LICAF, Diodes, Dye lasers, Erbium-Glass, Excimer lasers, etc. are examples of a pulsed-laser. High-class Continuous Working (CW) lasers, such as Nd:YAG, KTP and Diode lasers (at any wavelength between 630 and 1320 nm) are also known for their risk in causing blindness. Moreover, these lasers are at times used for cosmetic surgery in the vicinity of the eyes, such as for eyebrow removal or skin rejuvenation around the eyes, and therefore such surgery causes additional risk to eye damage. Other infrared lasers (pulsed and CW), such as diodes operatng at 1445 nm wavelength, $CO_2$ and Erbium, are also capable of causing severe eye damage from a distance by burning the cornea due to the strong absorption of laser beams emitted from such laser sources in the aqueous humor of the eyeball.

There is also a risk of hair and skin burns, if the laser units are mishandled, even if operated in remote locations. Should a collimated laser beam hit a flammable material in the treatment room, a fire may result.

The risks associated with coherent lasers do not stem only from the capability to generate highly collimated beams, but also from the capability to concentrate the entire laser energy onto a confined surface from a distance, with the appropriate focusing optics.

Due to the extremely high thermodynamic temperature of lasers as electromagnetic radiation sources, as compared to the much lower temperature of conventional non-coherent light sources, the efficacy of optical intensity preservation during the focusing or imaging of laser beams, is close to 100%. Conventional non-coherent light sources, although safe to use, cannot be imaged without substantial intensity loss.

All of the above-mentioned risks associated with visible and near infrared lasers have led to very strict governmental regulations regarding the operation of medical and aesthetic laser-based systems, causing a substantial increase in the expenses of both manufacturers and operators of these systems. According to some of these governmental regulations, the operation of laser devices/systems is restricted to trained and skilled personnel, i.e. technicians or nurses under the supervision of a physician. In many countries, non-medical personnel such as cosmeticians are not allowed to handle laser-based systems at all. As a result the laser cosmetic business volume is restricted to a small fraction of its potential volume.

According to some aspects of medical and cosmetic laser systems, the treatment is focused on selected targets at the outer surface of the skin or within the skin. Each of these targets, for example, hair, vascular lesions, pigmented lesions, tattoos, acne, mild collagen damages resulting in fine wrinkles, and sun-damaged skins, have different optical spectral absorption characteristics. Therefore, these applications utilize laser systems that are capable of generating visible or near infrared light having a wavelength within the range of 310–1600 nm. There exists, therefore, a risk of directing a laser beam having an incorrect wavelength to a selected treated organ/tissue, which may severely damage this organ/tissue. Even if the organ is treated by a laser beam having the correct wavelength, there is always a risk that the laser beam might be mistakenly aimed to other areas, which are highly sensitive to the selected wavelength, thereby resulting in damage.

As opposed to laser systems, non-laser incoherent diffused sources, such as Intense Pulsed Light (IPL) sources, which are based on high voltage arc lamps, are generally considered to be damage-safe from a distance, since IPL systems have a limited light source temperature, usually in the range of 1000–10,000° C., and are consequently of limited brightness and are not focusable to small spots, in contrast to as high as 1,000,000° C. in laser systems.

However, IPL systems have reduced spectral selectivity due to their broad spectral bands. Consequently, IPL-based systems offer rather limited treatment capabilities in comparison to laser-based systems.

U.S. Pat. No. 6,197,020 and U.S. Pat. No. 6,096,029 disclose imaging of a focusing, diffusing light plate, such as from the distal surface of a bundle of optical fibers at a distance beyond the system, in order to focus the beam below the tissue surface. The systems disclosed herein are also extremely risky to the eyes since the laser energy density is essentially preserved within a relatively small solid angle to which an eye may be exposed, even after having transporting the beam to a distal confined spot. As opposed to the present invention, these two patents conform to state of the art treatments by which the focusing of a laser beam to subcutaneous locations beyond the distal end of the treatment system is acceptable. The generation of a laser beam having a large divergent solid angle is disadvantageous, according to prior art methods, particularly since efficient imaging and focusing on the skin or into the skin would be precluded. Also, the laser energy density associated with these two patents is efficacious only when the diffusing, focusing plate is at a distance from a target, and is not efficacious when located adjacent to a target.

G. Vargas and A. J. Welch, in their article "Effects of Tissue Optical Clearing Agents on the Focusing Ability of Laser Light within Tissue" ("Lasers in Surgery and Medicine", Supplement 13, 2001, p. 26) describe techniques for reducing the scattering of light energy within a tissue, in order to provide for a more focused spot and, thus, more efficient treatment of dermal lesions. However, as already described, there is a trade-off between the efficiency of a laser device and the potential risk in its operation; i.e., as the beam is more focused, the treatment becomes more risky.

Other relevant prior art is disclosed in U.S. Pat. Nos. 5,595,568, 5,879,346, 5,226,907, 5,066,293, 5,312,395, 5,217,455, 4,976,709, 6,120,497, 5,411,502, 5,558,660, 5,655,547, 5,626,631, 5,344,418, 5,964,749, 4,736.743, 5,449,354, 5,527,308, 5,814,041, 5,595,568, 5,735,844, 5,057,104, 5,282,797, 6,011,890, 5,745,519, and 6,142,650.

The prior art laser units are not capable of generating a beam with a high energy level that may be used for aesthetic or surgical procedures without presenting a risk of injury to bystanders or damage to property, such as by igniting a fire.

It is an object of the present invention to provide a laser beam that may be used for aesthetic or surgical procedures.

It is an object of the present invention to provide a laser beam that overcomes the disadvantages of the prior art.

It is another object of the present invention to provide a laser beam that is not injurious to an operator, observer or to objects located in the vicinity of or at a distance from a target.

It is an additional object of the present invention to provide a laser beam that may be used for industrial applications.

It is yet another object of the present invention to provide a unit of optical elements that provides wide angle diffusion with high thermal durability Other objects and advantages of the invention will become apparent as the description proceeds.

SUMMARY OF THE INVENTION

The present invention comprises a method of improving bodily safety of bystanders exposed to a monochromatic light source, comprising: providing a monochromatic light source with a distal end, causing said monochromatic light to diverge at said distal end, whereby at a first position of said distal end relative to a target the energy density of an exit beam from said distal end is substantially equal to the energy density of the monochromatic light and at a second position of the distal end relative to a target the energy density of the light emitted from said distal end is significantly less than the energy density of the monochromatic light.

As referred to herein, monochromatic light is defined as being divergent when its exit angle from the distal end of the monochromatic light source, or from the distal end of a diverging unit, when used, is greater than a half angle of 6 degrees, wherein a "half angle" is defined as the half angle measured on a plane perpendicular to the propagation axis of a collimated beam generated by the monochromatic light source. With such a divergent angle, protective eyeglasses having an optical density approximately of only 2 are required for the aesthetc laser types specified hereinafter, corresponding to a transmittance of 1%. When the divergent half angle is 20 degrees, protective eyeglasses with an optical density of 1 are required, corresponding to a transmittance of 10%. When the divergent half angle is 60 degrees, no protective eyeglasses are required.

As referred to herein, "distal" is defined as a direction towards the exit of a monochromatic light source, or of a unit attached to the latter, when used, and "proximate" is defined as a direction opposite from a distal direction.

The method preferably further comprises the steps of:
a) providing a diverging unit transparent to the monochromatic light unit comprising at least one focusing lens, a plurality of reflectors and a distally positioned plate transparent to the monochromatic light;
b) attaching said diverging unit to the distal end of the monochromatic light source;
c) focusing the monochromatic light onto at least one of said reflectors; and
d) allowing light rays to exit said plate at varying angles, depending on the number of times reflected by said reflectors, whereby to cause said monochromatic light to be divergent.

In one preferred embodiment, the method further comprises the step of scattering the monochromatic light, said scattered monochromatic light being divergent.

As referred to herein, "scattered" monochromatic light is defined as light whose direction has randomly changed by reflection or refraction from discontinuities in the medium through which it propagates, without any substantial change in the wavelength of the incident light.

In one aspect, scattering is accomplished by
a) providing a diffusing unit with a distal end, said diffusing unit comprising at least one diffusively transmitting element, wherein each of said diffusively transmitting elements is transparent to the monochromatic light;
b) attaching said diffusing unit to the distal end of the monochromatic light source; and
c) allowing the monochromatic light to be scattered by each of said diffusively transmitting elements.

In another aspect, scattering is accomplished by
a) providing a diffusing unit transparent to the monochromatic light comprising an angular beam expander and at least one diffuser;
b) attaching said diffusing unit to the distal end of the monochromatic light source; and
c) allowing the monochromatic light to propagate through said angular beam expander and said at least one diffuser, whereby to scatter said monochromatic light.

In one aspect, scattering is accomplished by a) providing a diffusing unit with a plurality of diffusers, wherein at least one diffuser is axially displaceable;
b) axially displacing said at least one axially displaceable diffuser to an active position such that each diffuser is substantially in contact one with the other, whereby the energy density of an exit beam from said diffusing unit is substantially equal to the energy density of the monochromatic light at the first position of the distal end of the monochromatic light source; and
c) axially displacing said at least one axially displaceable diffuser to an inactive position such that each diffuser is separated one from the other by a gap large enough to generate a sufficiently large scattering angle such that the energy density of the light emitted from said diffusing unit at the second position of the distal end of the monochromatic light source is significantly less than the energy density of the monochromatic light.

Preferably, the first position of the distal end of the monochromatic light source is substantially in contact with a target to which the monochromatic light is directed.

In one aspect, the radiance of the divergent monochromatic light is less than 14 $J/cm^2/sr$. In another aspect, the radiance of the divergent monochromatic light is less than $10*k1*k2*(t^{1/3})$ $J/cm^2/sr$, where t is a laser pulse duration in seconds, $k1=k2=1$ for a wavelength ranging from 400 to 700 nm, $k1=1.25$ and $k2=1$ for a wavelength of approximately 750 nm, $k1=1.6$ and $k2=1$ for a wavelength of approximately 810 nm, $k1=3$ and $k2=1$ for a wavelength of approximately 940 nm, and $k1=5$ and $k2=1$ for a wavelength ranging from 1060 to 1400 nm.

As referred to herein, "radiance" is defined as the energy density divided by solid angle, wherein energy density is radiant energy per projected area. The value of a solid angle is given in units of steradians, normally symbolized as "sr."

The method further comprises measuring the radiance of the divergent monochromatic light and issuing a warning as a result of a mishap if the radiance of the divergent monochromatic light is greater than a predetermined safe value.

The monochromatic light is selected from the group of collimated laser beam, convergent laser beam, concentrated multiple laser beams and fiber guided laser beam.

The monochromatic light source is selected from the group of Excimer, Dye, Nd:YAG 1064, 1320 and 1440 nm, frequency doubled Nd:YAG, Ruby, Alexandrite, Diode including diodes operating at a wavelength of 810 to 830 nm, 940 nm, and 1450 nm, stack of diodes, LICAF, Er:Glass, Er:YAG, Er:YSGG, $CO_2$, isotopic $CO_2$ and Holmium lasers.

The monochromatic light is provided with a wavelength ranging from 308 to 1600 nm or between 1750 nm to 11.5 microns and the energy density level of the monochromatic light source ranges from 0.01 to 2000 $J/cm^2$.

In one aspect, the monochromatic light source is a plurality of monochromatic diodes.

The bodily safety includes eye safety, skin safety and environmental safety.

The exit beam at the first position is used in applications selected from the group of cosmetic applications, medical applications and industrial applications.

The exit beam at the first position is used in applications selected from the group of hair removal, coagulation of blood vessels located on a face or legs, treatment of rosacea, tattoo removal, removal of pigmented lesions in the skin, skin rejuvenation, treatment of psoriasis, treatment of acne, skin resurfacing, skin vaporization, collagen contraction, dental applications, removal of pigments from the gums, teeth whitening, dermatology, gynecology, podiatry, urology, reduction of pain, laser welding of transparent plastic materials, surface treating of materials, laser annealing, evaporation of paint and ink stains and cleaning of buildings, stones, antique sculptures and pottery.

In one aspect, a laser beam is controllably repositionable to scan targets of the diffusively transmitting element, wherein the sequence of targets to be impinged by the laser beam is programmable.

The duration of a laser pulse ranges from 1 nanosecond to 1500 msec, and the diameter of a spot size ranges from 1 to 20 mm. If so desired, a series of pulses is generated.

The present invention also comprises a method for converting a laser unit suitable for aesthetic treatment, medical treatment or industrial treatment into an eye safe laser unit, comprising attaching a diverging optical unit to the distal end of a laser unit, allowing monochromatic light to propagate through said unit, generating a non-coherent and extended diffused source of light from said unit at a sufficiently low radiance value such that said source of light is eye safe to bystanders exposed to a monochromatic light source and of a sufficiently high energy density at a treatment location to effect said aesthetic treatment, medical treatment or industrial treatment.

In one aspect, the unit is a divergent diffusing optical unit.

The present invention also comprises a method of cooling skin which is irradiated with monochromatic light, comprising:
a) providing a monochromatic light source with a distal end;
b) providing a unit with two transmitting elements that are transparent to monochromatic light, such that a gap is formed between said two elements;
c) attaching said unit to the distal end of the monochromatic light source;
d) placing said unit on a skin location to be treated;
e) providing means for skin cooling, said skin cooling means being disposed within said gap;
f) allowing monochromatic light to propagate through said unit to said skin location, the temperature of the skin location to be treated thereby increasing; and
g) allowing said skin cooling means to cool said skin location.

The method preferably further comprises the following steps:
a) providing the unit with a diffusively transmitting element and with a clear transmitting element distally positioned with respect to said diffusively transmitting element;
b) allowing the monochromatic light to be scattered by said diffusively transmitting element, whereby the energy density of an exit beam from said clear transmitting element is substantially equal to the energy density of the monochromatic light; and
c) repositioning the unit from the target to a predetermined position at which the energy density of an exit beam from said diffusively transmitting element is significantly less than the energy density of the monochromatic light.

In one aspect, the skin cooling means is fluid transparent to the monochromatic light, said fluid flowing through a conduit inserted within the gap. The fluid may be in fluid communication with an external cooler.

In another aspect, the skin cooling means is a thermoelectric cooler, the thermoelectric cooler operative to cool the lateral sides of the transmission element placed on the skin location to be treated.

The present invention also comprises a method of improving eye safety during exposure to a monochromatic light source, comprising: providing a monochromatic light source and generating a visible flash prior to the emission of a pulse of monochromatic light, thereby inducing an eye of a bystander to blink or to change its field of view in order to avoid staring at the monochromatic light.

Preferably, the generation of the visible flash is synchronized to the timing of the emission of the monochromatic light pulse, wherein the duration of the pulse is shorter than an eye blinking response time.

The monochromatic light source is suitable for hair removal, photorejuvenation or treatment of vascular lesions.

The present invention comprises an apparatus for improving bodily safety of bystanders exposed to a monochromatic light source, comprising a means attached to the distal end of a monochromatic light source, said means adapted to cause the monochromatic light to be divergent, whereby at a first position of said distal end relative to a target the energy density of an exit beam from said distal end is substantially equal to the energy density of the monochromatic light and at a second position of said distal end relative to a target the energy density of the light emitted from said distal end is significantly less than the energy density of the monochromatic light.

In one aspect, the diverging means comprises a diverging unit provided with at least one focusing lens, a plurality of reflectors and a distally positioned plate transparent to the monochromatic light, each of said at least one lens provided with a suitable focal length so as to focus the monochromatic light onto at least one of said reflectors, each of said reflectors positioned so as to allow light rays to exit said plate at varying angles, depending on the number of times reflected by said plurality of reflectors, whereby to cause said monochromatic light to be divergent.

In one embodiment, the diverging means is also a scattering means.

In one aspect, the scattering means comprises a diffusing unit attachable to the distal end of the monochromatic light source, said diffusing unit including at least one diffusively transmitting element that is transparent to essentially coherent monochromatic light.

The material of each diffusively transmitting element is selected from the group of silica, glass, sapphire, diamond, non-absorbing polymer, light diffusing polymer, polycarbonate, acrylic, densely packed fibers, NaCl, $CaF_2$, glass, ZnSe and $BaF_2$.

In one aspect, the diffusing unit is further provided with a clear transmitting element distal to a diffusively transmitting element, the diffusively transmitting element and clear transmitting elements being mutually parallel and perpendicular to the longitudinal axis of the diffusing unit.

The clear transmitting element is made of a material selected from the group of glass, sapphire, transparent polymer including polycarbonate and acrylic, $BaF_2$, NaCl and $ZnF_2$.

A gap between the diffusively transmitting and clear transmitting elements is preferably less than 2 mm.

Each diffusively transmitting element may be provided with a plurality of irregularities which are randomly distributed thereabout.

The diffusively transmitting element may also be formed by a diffraction pattern or by a randomly distributed array of thin fibers.

In another aspect, the scattering means comprises a diffusing unit attachable to the distal end of the monochromatic light source, said diffusing unit including an angular beam expander and at least one diffuser.

An angular beam expander preferably comprises at least one light guide, each of said light guides being provided with internally reflecting walls and an exit surface. A light guide is made of a material selected from the group of solid glass, sapphire, plastic and liquid dielectric material, and may be tapered.

An angular beam expander may also comprise an optical element which increases the divergence angle of monochromatic light and a diffuser which receives light from said optical element and emits said received light to the light guide, the exit surface of said light guide functioning as a wide angle extended diffuser source.

In another aspect, the scattering means comprises a diffusing unit attachable to the distal end of the monochromatic light source, said diffusing unit comprising a plurality of diffusers wherein at least one is axially displaceable, such that at an active position the plurality of diffusers are substantially in contact one with the other at the first position of the distal end of the monochromatic light source, and the energy density of an exit beam from said diffusing unit is substantially equal to the energy density of the monochromatic light, and at an inactive position each of said diffusers is separated one from the other by a gap such that the energy density of the light emitted from the diffusing unit is significantly less than the energy density of the monochromatic light at the second position of the distal end of the diffusing unit.

The duration of a laser pulse ranges from 1 nanosecond to 1500 msec.

A laser unit is provided with a power level ranging from 1 to 2000 W, when under continuously working operation.

In one aspect, the apparatus further comprises a plurality of reflectors, the angular disposition and distance of each reflector relative to the diffusing unit being repositionable, whereby to accurately direct the monochromatic light to a selected target on the diffusively transmitting element. A processor is preferably provided, said processor suitable for the programming of the sequence of targets to be impinged by the monochromatic light. A scanner is also preferably provided for rapid repositioning of the monochromatic light to a target on the diffusively transmitting element.

In one aspect, the distance between a distal end of the diverging means and the target at the first position of the distal end of the monochromatic light source is the smaller of 2 mm and the diameter of the monochromatic light.

A diffusing or diverging unit is attached to the distal end of the monochromatic light source by an attachment means.

In one aspect, the unit is fixedly attached to the distal end of the monochromatic light source.

In one aspect, the unit is integrally formed together with the distal end of the monochromatic light source during manufacturing, the unit being disposed internally to the outer wall of the monochromatic light source.

In another aspect, the attachment means is releasable. For example, the attachment means is permanently attached to the monochromatic light source and displaceable, whereby in one position of a displaceable unit the monochromatic light source is coherent, not propagating through said displaceable unit, and in a second position at which said displaceable unit is attached to the distal end of the monochromatic light source, the monochromatic light is noncoherent, propagating through the displaceable unit.

Preferably, the apparatus further comprises a means to evacuate vapors or particles from a target to thereby prevent a change in optical properties of the unit. The evacuation means is U-shaped in vertical cross-transmission element, to allow for contact with a target at its lateral ends and for evacuation of vapors or particles through a gap formed by its central open region.

In one aspect, the evacuation means further comprising a relay optics device, whereby to concentrate the exit beam from the unit onto the target.

The present invention also comprises an apparatus for cooling skin which is irradiated with monochromatic light, comprising:
a) a monochromatic light source with a distal end;
b) a unit attachable to the distal end of the monochromatic light source, said unit being provided with two elements that are transparent to monochromatic light, such that a gap is formed between said two elements; and
c) a means for skin cooling insertable within said gap, said skin cooling means adapted to reduce the rate of increase of temperature at a target skin location.

In one aspect, one element is a diffusively transmitting element and the other element is a clear transmitting element distally positioned with respect to said diffusively transmitting element, whereby the energy density of an exit beam from the diffusing unit is substantially equal to the energy density of the monochromatic light upon placement of the diffusing unit at a position adjacent to a target skin location and is significantly less than the energy density of the monochromatic light at a distance from said target.

In one aspect, the skin cooling means is a fluid transparent to said monochromatic light, said fluid flowable through a conduit inserted within the gap. Preferably, the fluid is in fluid communication with an external cooler.

In one aspect, the fluid is a liquid or a gas.

In another aspect, the skin cooling means is a thermoelectric cooler, the thermoelectric cooler operative to cool the lateral sides of the element placed adjacent to the skin location to be treated.

In another aspect, the apparatus comprises a scanner, said scanner being adapted to rapidly reposition the monochromatic light to a target on the diffusively transmitting element, the skin cooling means capable of continuously cooling the skin at a corresponding target skin location.

The present invention also comprises an apparatus for improving eye safety during exposure to a monochromatic light source, comprising: a monochromatic light source, a means for generating a visible flash prior to emission of a monochromatic light, and control circuitry in communication with said means for generating a visible flash.

The control circuitry is preferably synchronized such that the flash is generated prior to the emission of each pulse of monochromatic light, thereby inducing an eye of a bystander to blink or to change its field of view in order to avoid staring at the monochromatic light.

The duration of the pulse is preferably shorter than an eye blinking response time.

BRIEF DESCRIPTION OF THE DRAWINGS

In the drawings:

FIG. 1 illustrates a side view of various laser units equipped with a diffusing unit, in accordance with the present invention, wherein the delivery system shown in FIG. 1a is an articulated arm, in FIG. 1b is an optical fiber and in FIG. 1c is a conical light guide;

FIG. 3 is a schematic diagram of various configurations of prior art laser units, wherein

FIG. 4 is a schematic diagram illustrating the advantages of employing a diffusing unit of the present invention, wherein

FIG. 5 is a schematic drawing showing the propagation of a laser beam towards a blood vessel, wherein FIG. 5a shows the propagation of an unscattered laser beam towards a blood vessel, FIG. 5b shows the propagation of a scattered laser beam towards a blood vessel, FIG. 5c illustrates the formation of an ablation by means of an unscattered laser beam. FIG. 5d illustrates the formation of an ablation by means of a scattered laser beam in accordance with the present invention, and FIG. 5e illustrates the scattering of a laser beam distant from a blood vessel;

FIG. 7 illustrates the production of a plurality of microlenses, wherein

FIG. 8 illustrates two types of a diffusing unit, wherein

FIG. 10 illustrates a diffusing unit which utilizes an angular beam expander without a light guide in FIG. 10a and with a light guide in FIG. 10b;

FIG. 12 illustrates a diffusing unit which includes two diffusers, one of which is axially displaceable, wherein

FIG. 14 is another preferred embodiment of the present invention in which a non-scattering diverging unit is used to diverge an input laser beam, wherein

FIG. 15 is a schematic diagram of various means of cooling skin during laser-assisted cosmetic surgery, wherein FIGS. 15a–d are prior art means, while FIG. 15e utilizes cooling fluid and FIG. 15f utilizes a thermoelectric cooler;

FIG. 17 is a schematic drawing of a flashing device, wherein

DETAILED DESCRIPTION OF PREFERRED EMBODIMENTS

Figure 2A:
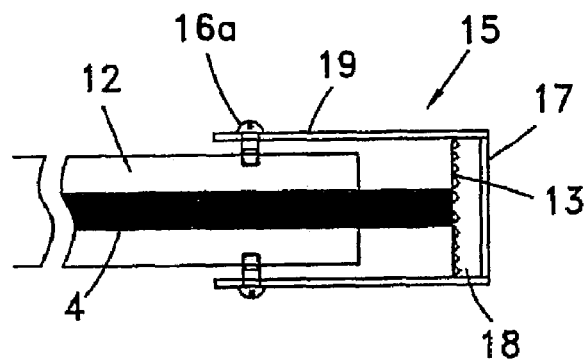
FIG. 2 illustrates a side view of the distal end of a laser unit, showing how the diffusing unit is attached thereto, wherein the diffusing unit is externally attached to the guide tube in FIG. 2a, is attached to a pointer in FIG. 2b, is releasably attached to the guide tube in FIG. 2c, is integrally formed together with the guide tube in FIG. 2d and is displaceable in FIG. 2e whereby at one position the exit beam propagates therethrough and at a second position the exit beam does not propagate therethrough.
Figure 2B:
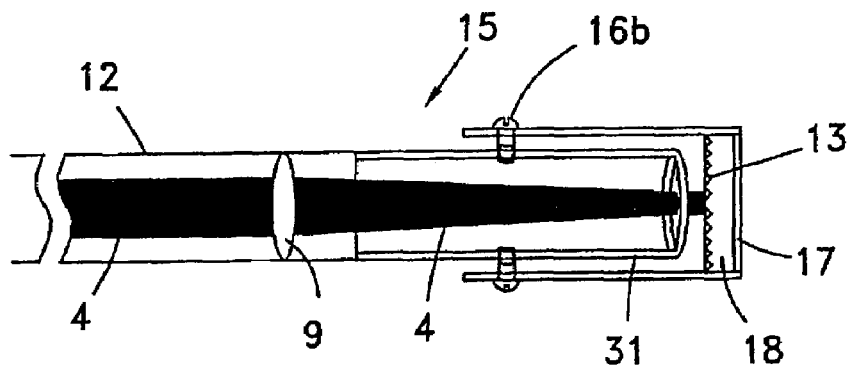
Figure 2C:
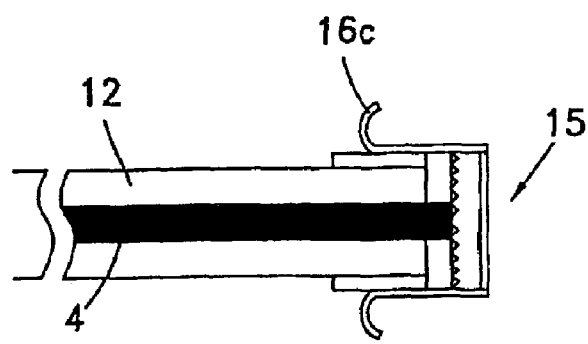
Figure 2D:
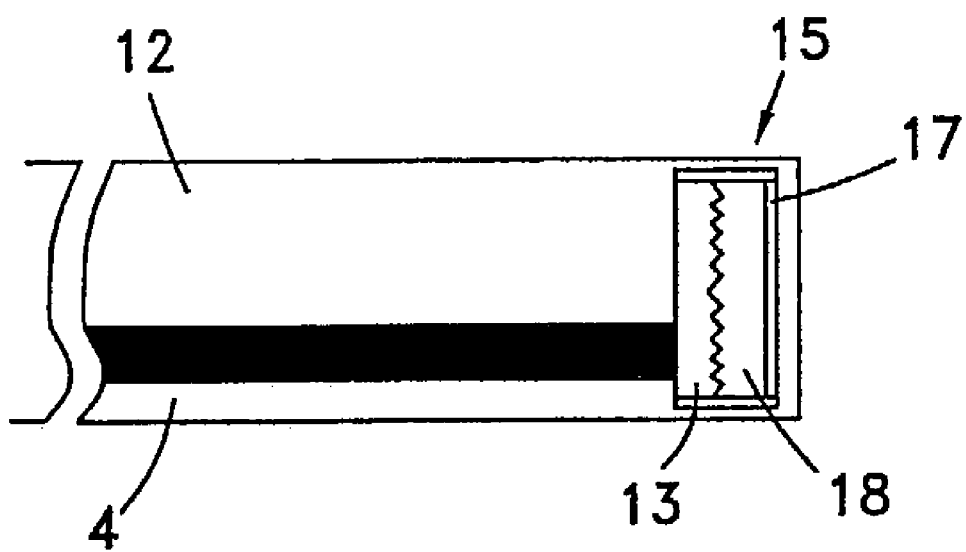
Figure 2E:
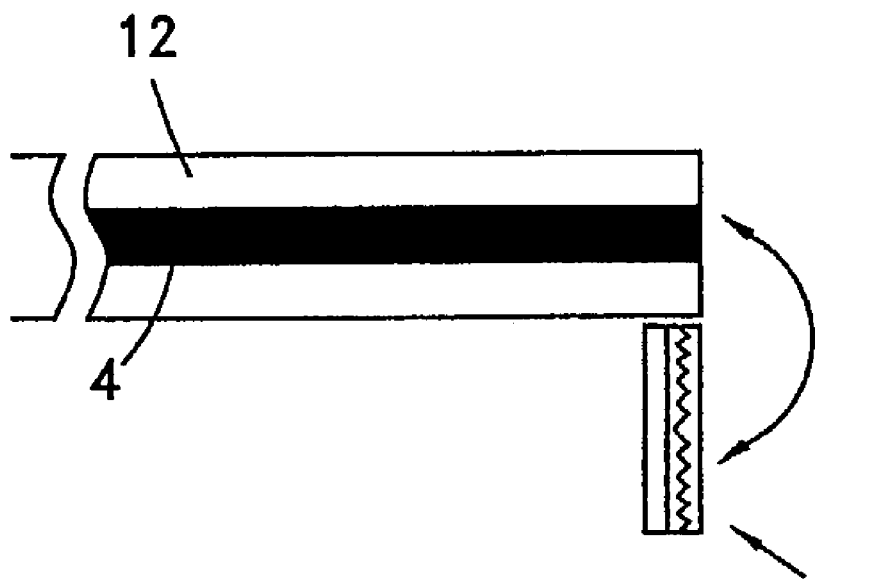

FIG. 1a illustrates a high-intensity laser unit, generally designated by 10, which is suitable for use with the present invention. Laser unit 10 operates at a wavelength ranging between 300 and 1600 nm or between 1750 nm and 11.5 microns, either pulsed, with a pulse duration of 1 nanosecond to 1500 milliseconds and an energy density of 0.01–200 J/cm$^2$, or continuous working with a power density higher than 1 W/cm$^2$. Laser unit is provided with a diffusing unit, generally designated by 15, which induces the exit beam to be scattered. An exit beam is considered to be scattered according to this embodiment when its average half angle angular divergence is greater than 42 degrees relative to the propagation axis of collimated beam 4. A half angle of 60 degrees corresponds to the half angle generated by an "ideal transmitting diffuser," which herein refers to a diffuser with 100% transmission and is provided with Lambertian angular scattering properties. Such a scattering angle, in accordance with the present invention, allows the light which exits diffusing unit 15 to be safe to the eyes of a bystander, yet is provided with a sufficiently high energy density which is necessary for the clinical efficacy of the laser unit.

Laser unit 10 comprises amplifying medium 1 activated by power supply 2 for increasing the intensity of a light beam and two parallel mirrors 3 that provide feedback of the amplified beam into the amplifying medium, thereby generating a coherent beam of ultrapure frequency. The laser unit emits a coherent beam 4 which propagates through a delivery system 5 to distal end 6. The delivery system depicted in FIG. 1a is articulated arm 7a. Diffusing unit 15 is fixedly attached to the distal end of guidance tube 12 by attachment means 16, which may be a set of screws or by bonding or other means known to those skilled in the art, thereby inducing noncoherent randomly scattered beam 14 associated with a narrow spectral bandwidth that does not present any risk of damage to bodily tissue if the laser is inadvertently directed to an incorrect target. The diffusing unit includes a passive refractive element that preserves the wavelength of coherent beam 4, as well as its narrow bandwidth, which is generally less than one Angstrom.

In one preferred embodiment of the invention, diffusing unit 15 is preferably cylindrical or rectangular, although any other geometrical shape is equally suitable, and comprises diffusively transmitting element 13, which is proximate to distal end 6 of the laser unit and clear transmitting element 17. Both diffusively transmitting element 13 and clear transmitting element 17 have the same dimensions and are bonded to diffusing unit 15. Diffusively transmitting element 13 and clear transmitting element 17 are preferably separated by narrow gap 18. Due to the existence of gap 18, the laser beam will remain scattered even if clear transmitting element 17 shatters, thereby preserving the inherent safety of a laser unit that incorporates the present invention. The width of gap 18 is as small as possible, usually 0.1 mm. However, diffusing unit 15 may be adapted to a configuration in which diffusively transmitting element 13 contacts clear transmitting element 17. Alternatively, diffusing unit may be provided without a clear transmitting element, whereby the frosted surface of diffusively transmitting element 13 faces the laser unit and its smooth surface faces the tissue.

Scattering is achieved by means of minute irregularities of a non-uniform diameter formed on the substrate of diffusively transmitting element 13. Diffusively transmitting element 13 is preferably produced from thin sand blasted or chemically etched glass, e.g. having a thickness from 0.1 to 0.2 mm, or a thin sheet of non-absorbing light diffusing polymer, e.g. having a thickness of less than 50 microns, such as light diffusing polycarbonate, Mylar or acrylic.

A diffusively transmitting element may also be produced by using a large angle holographic diffuser such as one produced by Physical Optics Corporation (PCO), USA, and is placed adjacent to an additional diffuser. A holographic diffuser illustrated in FIG. 11 induces a scattering half angle, for example, of at least 40 degrees and the second diffuser additionally induces the scattering so as to attain a scattering half angle of e.g. 60 degrees.

Figure 9A:
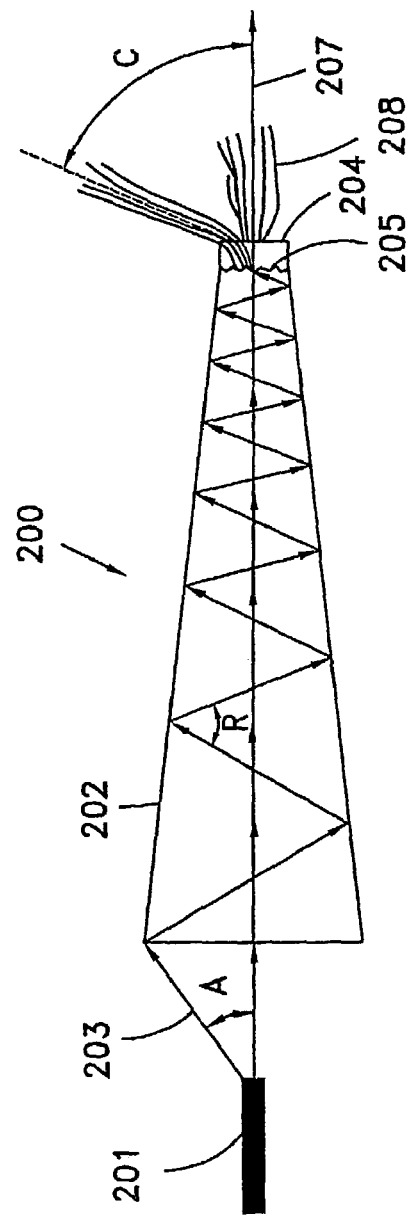
FIG. 9 illustrates a diffusing unit which employs a tapered light guide, such that the light guide receives monochromatic light from an optical fiber in FIG. 9a and from an array of microlenses in FIG. 9b.
Figure 9B:
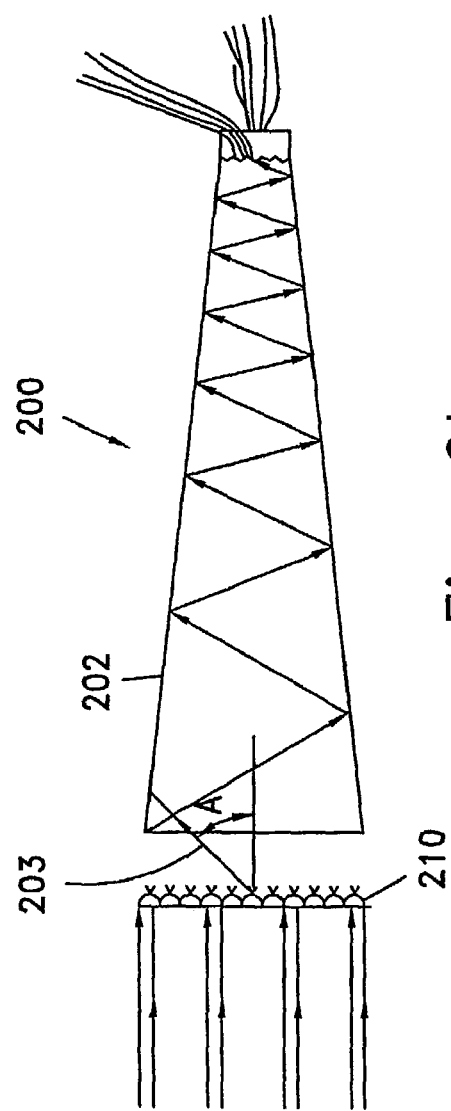

A diffuser which approaches an ideal transmitting diffuser and induces a scattering half angle of 60 degrees and a scattering solid angle of 3.14 sr may be produced from material such as acrylic or polycarbonate by pressing the material against an appropriate surface provided with a very dense array of Fresnel microlenses, such as those produced by Fresnel Technologies Inc., USA, or by placing arrays of microlenses surfaces separated from a light guide as depicted in FIG. 9b.

Similarly diffusively transmitting element 13 may be produced from light diffusing paper such as transparent "Pergament" drawing paper, and may also be produced from other materials such as ZnSe, BaF$_2$, and NaCl, depending on the application and the type of laser used. Both faces of clear transmitting element 17 are essentially planar and smooth. Clear transmitting element 17, which is capable of withstanding the thermal stress imposed by a scattered laser beam, is transparent and made from sapphire, glass, a polymer such as polycarbonate or acrylic, and may be produced from other materials as well, such as ZnF$_2$.

Diffusively transmitting element 13 may be chilled so that it will be capable of withstanding the high power densities which are necessary for attaining clinical efficacy.

As depicted in FIG. 1b, the delivery system may also be optical fiber 7b into which laser beam 4 is focused Diffusing unit 15 is mounted on guidance tube 8, which directs the beam exiting the distal end of optical fiber 7b by attachment means 16. Furthermore, as depicted in FIG. 1c, the laser unit may be comprised of array 11 of miniature lasers, such as those provided with high power diode lasers, e.g. the Lightsheer produced by Coherent, USA, for hair removal. The beam delivery system for this configuration is preferably conical reflector 7c. In this configuration, diffusing unit 15 is fixed to distal end 6 of light guide 7c and transforms a high-risk beam into randomly scattered beam 14.

FIG. 2 illustrates various methods by which diffusing unit 15 is attached to a laser unit. In FIG. 2a, bracket 19 which supports diffusing unit 15 is attached to guidance tube 12 of an existing laser unit, such as one in use in a clinic, by attachment means 16a, which may be a set of screws or by bonding. As shown in FIG. 2b the laser unit is provided with pointer 31, or any other equivalent subdiffusing unit which enables the user to direct beam 4 to a desired target on the skin, by the focal length and beam diameter which are dictated by lens 9 mounted within guidance tube 12. In this alternative, diffusing unit 15 may be externally attached to guidance tube 12, or may be attached to pointer 19. In FIG. 2c, diffusing unit 15 is attached to Velcro tape 16c, or another type of adhesive tape. This type of attachment means is sufficient for temporary usage. In FIG. 2d, diffusing unit 15 is integrally formed together with guidance tube 12 during manufacturing, internal to the outer wall thereof. FIG. 2e illustrates a releasable attachment means, whereby in one position of a displaceable diffusing unit the exit beam is coherent, not propagating through a diffusively transmitting element, and in a second position in which diffusing unit 15 is attached to guidance tube 12, the exit beam is noncoherent and propagates through a diffusively transmitting element.

Figures 3A, 3B:
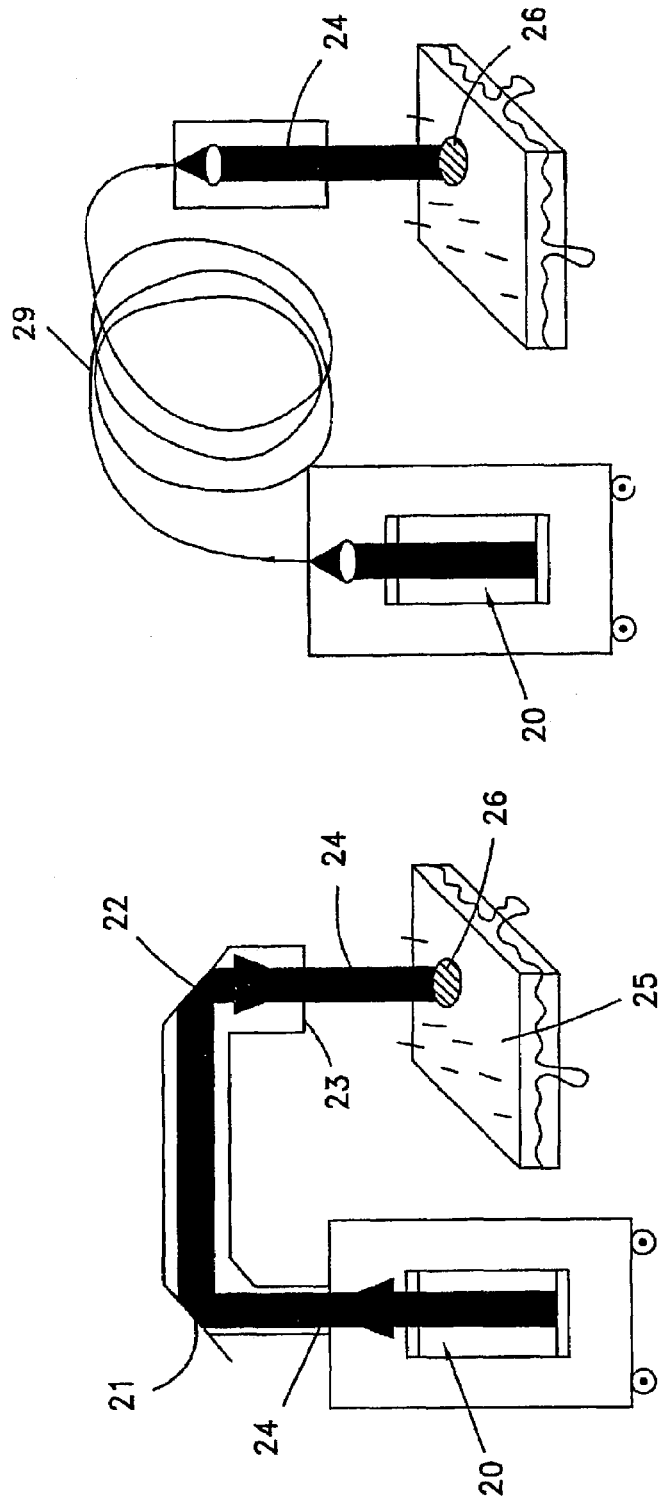
FIG. 3a shows a non-scattered beam directed by reflectors to a target.
FIG. 3b shows a non-scattered beam directed by an optical fiber to a target.
Figures 3C, 3D:
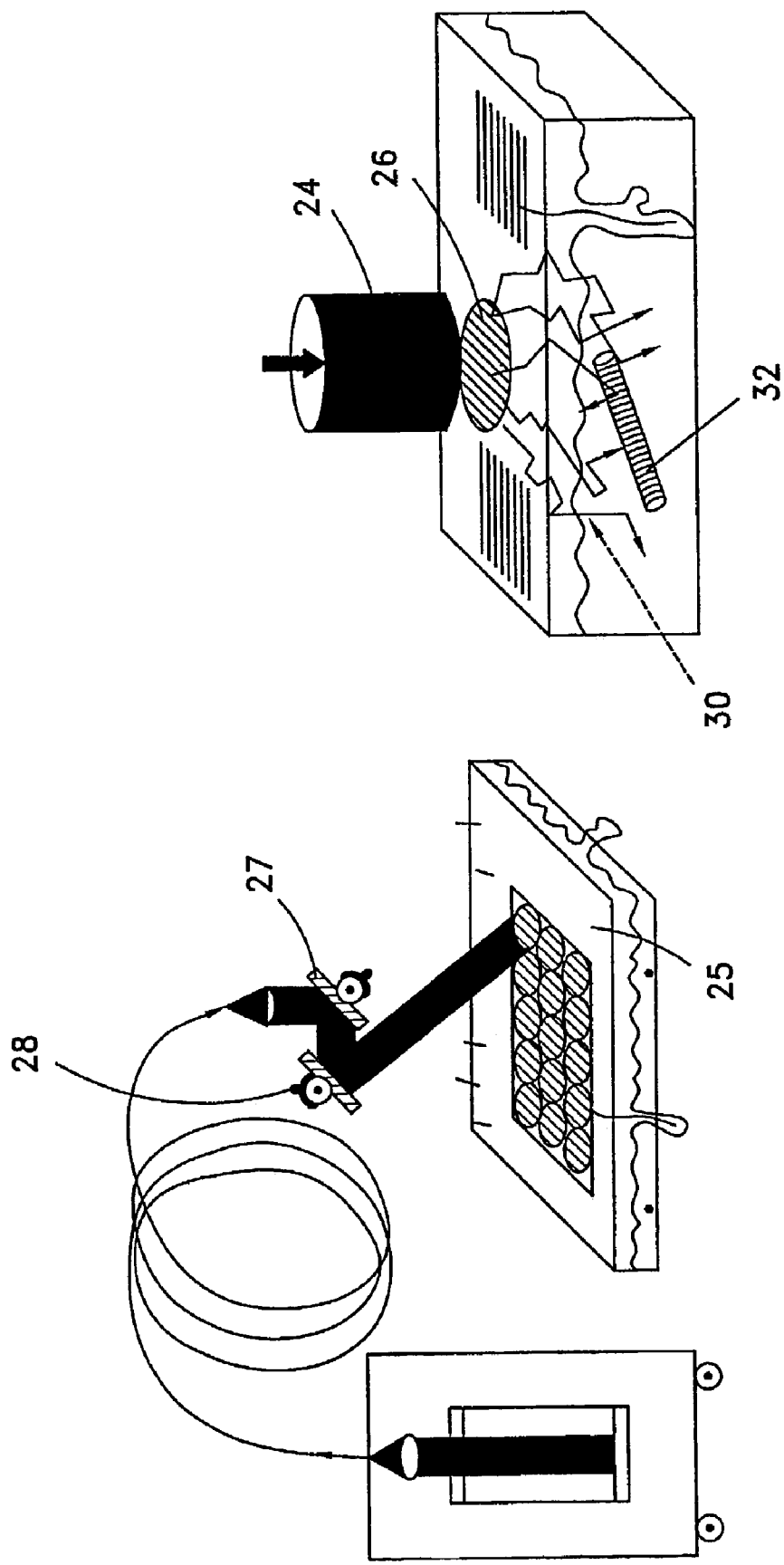
FIG. 3c illustrates prior art laser surgery performed with a laser beam and scanner.
FIG. 3d shows the propagation of prior art refracted laser beams towards a blood vessel.
Figure 3F:
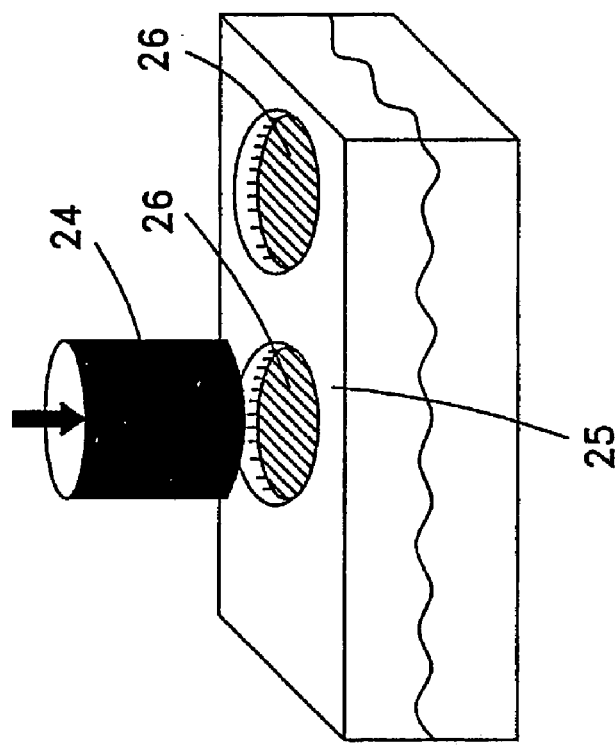
FIG. 3f shows the formation of a crater in tissue by an ablative beam.
Figure 3E:
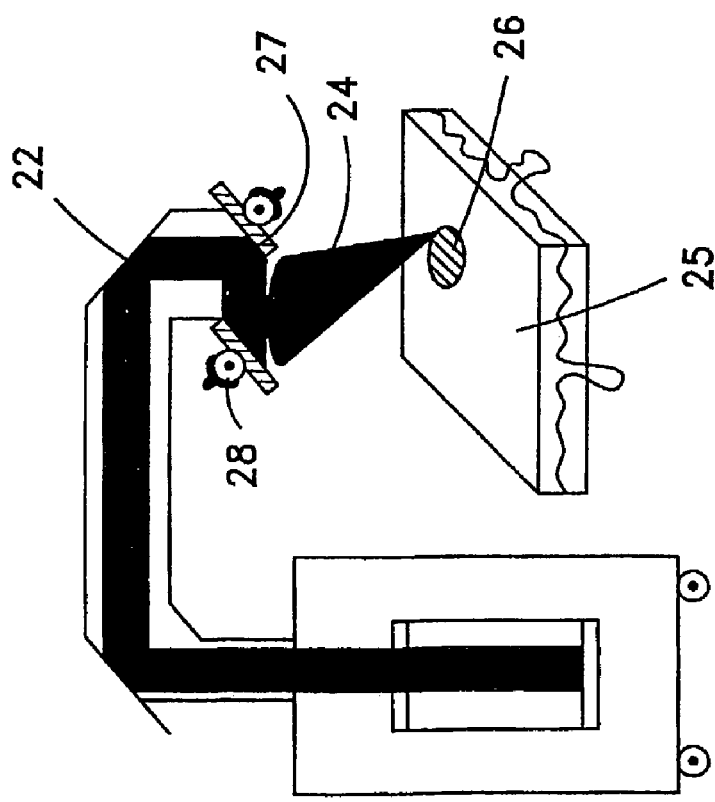
FIG. 3e shows an ablative laser beam focused on tissue in conjunction with a scanner.
Figure 4A:
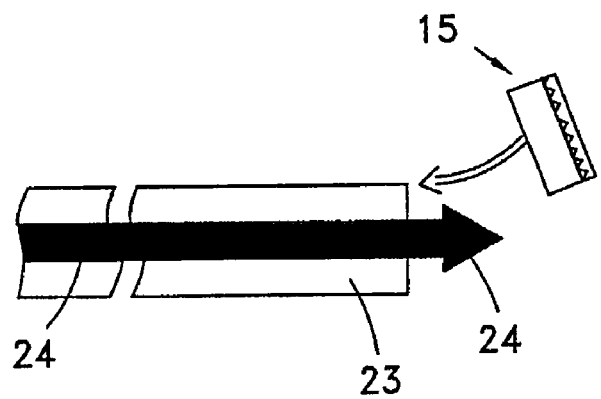
FIG. 4a shows the relative location of the diffusing unit.
Figure 4B:
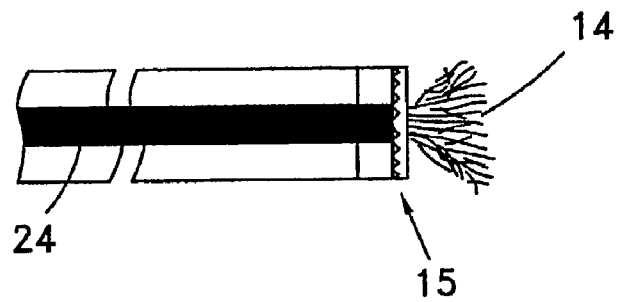
FIG. 4b shows that a collimated laser beam is transformed into a randomly scattered beam.
Figure 4C:
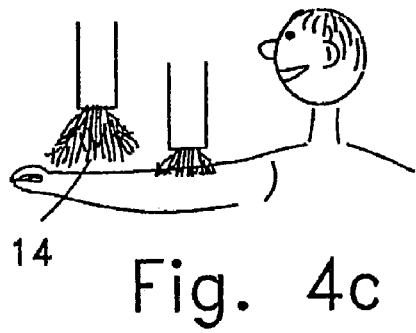
FIG. 4c shows that a scattered beam reduces risk of injury to the skin and FIG. 4d shows that a collimated laser beam reduces risk of injury to the eyes.
Figure 4D:
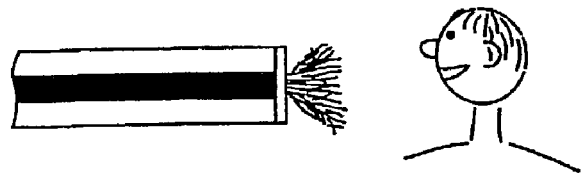

In prior art cosmetic laser surgery, as shown in FIG. 3a, laser unit 20 emits a non-scattered coherent beam 24 from distal end 23 via reflectors 21, 22, by optical fiber 29 in FIG. 3b, or alternatively by deflectors 27 as shown in FIG. 3c, to site 26 that is to be treated within tissue 25. Following the surgery, a well-defined spot is generally produced having a size of up to 20 mm, depending on the specific application and device. Furthermore, beam 24 may be directed by means of motor 28 as shown in FIG. 3c in those situations in which extensive surgery is desired and tissue 25 needs to be scanned. When the wavelength ranges from 310–1600 nm, i.e. ultraviolet and near-infrared, the beam is scattered into individual rays 30, as shown in FIG. 3d, while propagating to blood vessel 32 from site 26. Blood vessel 32 is presented as an example and could be replaced by a hair follicle or any type of skin lesion At wavelengths ranging from 1750 nm to 11.5 microns, i.e. far infrared, lasers are often used in focused pin-point ablation, that is, having a diameter ranging from 50–200 microns at a shallow depth of 20–150 microns, of epidermal or papillary dermal tissue in conjunction with a scanner, as shown in FIG. 3e. The lasers are used mainly for ablation of tissue, the formation of a crater shown in FIG. 3f. Laser 20, which is capable of effecting the desired surgery at a large distance between distal end 23 and target site 26 for the various applications shown in FIGS. 3a–d, nevertheless can cause severe damage if the beam is not properly aimed.

In contrast, the present invention, which is schematically depicted in FIG. 4, presents a much lower risk to the patient and to observers. As shown in FIG. 4a, diffusing unit 15 is attached to distal end 23 of the laser unit. Diffusing unit 15 transforms the coherent, usually collimated laser beam 24 into homogeneous, randomly scattered beam 14 shown in FIG. 4b. As a result beam 14 significantly reduces risk of injury to the skin as shown in FIG. 4c or to the eyes as shown in FIG. 4d since a collimated beam is not directed to these parts of the body. At very short distances of less than one tenth of the diameter of beam 24 from distal end 23, beam 24 has not begun to completely scatter and increase its diameter and is therefore efficacious as a means for performing cosmetic surgery as shown/in FIG. 4c, although an increase in the laser power level may sometimes be needed to compennsate for reverse reflections from the diffusing unit into the laser unit. Compensation, in terms of an increase in the needed power level for the laser unit, for reverse reflections is usually be close to 16% due to four air-glass interfaces with 4% Fresnel reflection, and at times may attain 50%. An anti-reflection coating may be used to reduce reflection. For laser units which operate at approximately 10–20% of their maximum energy capacity, it is possible to place the exit plane of the diffusing unit, whether a frosted or clear transmitting element, at a distance from the skin corresponding to approximately 50% of the exit beam diameter.

FIG. 5 demonstrates the advantages of the present invention. FIG. 5a illustrates conventional coherent laser beam 24 at a wavelength of 308 to 1600 nm. The collimated beam contacts tissue 25 at a diameter of D before being scattered into individual rays 30 during propagation to target destination 32. FIG. 5b illustrates the result of attaching diffusing unit 15 to the laser unit. When diffusing unit 15 is disposed at a small distance from the tissue surface, the diameter of the scattered beam which contacts tissue 25 is increased by a negligible value of Δd, assuming uniform scattering, in comparison with the original beam diameter of D. If the thickness t of diffusing unit 15 is less than one-tenth of original beam diameter D, there will be a loss of less than 20 percent in the original beam energy density. Also, the refraction angle θ, corresponding to an index of refraction of 1.5 for keratin, into the tissue relative to collimated beam 24, when a gap exists between diffusively transmitting element 13 and clear transmitting element 17, will never exceed the critical angle of 42 degrees. At a refraction angle less than this critical value, possible additional scattering in tissue is minimized. Consequently light intensity within the tissue is preserved, therefore generally retaining the clinical efficacy, i.e. the ability to perform a surgical or cosmetic procedure, of the laser unit.

Just as superficial ablation 29 is formed in tissue 25 as a result of a high energy density beam in the 1.8 to 11.5 micrometer spectral range as shown in FIG. 5c, a similar ablation may be formed in tissue 25 with the use of diffusing unit 15, with the addition of Δd, as shown in FIG. 5d. A thin spacer (not shown) may be advantageously added in order to evacuate vapors or smoke that has been produced during the vaporization process. Such a spacer is e.g. U-shaped in vertical cross-transmission element, to allow for contact with a target at its lateral ends and for vapor evacuation along the gap formed by its central open region. For surgical procedures with which a very fast ablation rate is needed, e.g. 1 $cm^3$/sec for a skin thickness of 0.1 cm, the spacer is necessarily relatively thick and the gap between the ablated tissue and the diffusing unit is relatively large, e.g. approximately 20–30 mm.

When an excessive amount of smoke is produced and the exit beam becomes diffracted before impinging on the tissue, it may be necessary to add a relay optics device (not shown), which regenerates the degraded exit beam between the diffusing unit and the tissue. An optical regenerator is provided with an internal coating, such that a new and stronger beam with the same characteristics as the degraded beam is produced when the coating emits light energy when stimulated by the incoming photons of the degraded beam. Cylindrical or conical tubes internally coated with gold with an inlet diameter equal to the exit diameter of the diffusing unit are exemplary optical regenerators for this application A small smoke evacuation port is preferably drilled in the wall of the tube.

When a long-wavelength laser, which does not focus on an eye retina and ranges from approximately 1345 nm to 10.6 microns, is employed, an diffusing unit may not be needed. To scatter the exit beam, an element may be externally attached to a surface which is in contact with the skin during a cosmetic or surgical procedure, so that the exit beam will diverge to a large extent and ensure eye safety from a distance of a few cm from a target, while the energy density is sufficiently high enough to allow for clinical efficacy. For example, a miniature 0.21 Joule/pulse Erbium laser, which produces a spot size of 1 mm$^2$ and generates an energy density of 2.1 J/cm$^2$, greater than the threshold for tissue ablation, will be safe to the eyes from a distance of 10 cm from a target if the beam has a divergence half angle of 45 degrees.

While the laser is an effective surgical tool when the diffusing unit is very close to the tissue surface, safety is ensured after the diffusing unit is repositioned so that it is disposed at a distance of a few millimeters, depending on the laser energy, from the tissue surface. As shown in FIG. 5e, the energy density of scattered beam 14 which impinges upon the surface of tissue 25 is much less than the energy density which results when the diffusing unit is proximate to the tissue surface.

Figure 6A:
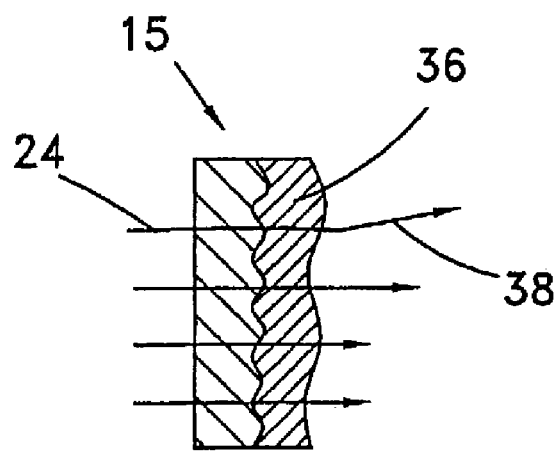
FIG. 6a is a schematic drawing showing the accumulation of liquid residue on a diffusively transmitting element and FIG. 6b is a schematic drawing in which a diffusively transmitting element is shown to be mounted within a hermetically sealed diffusing unit.

The diffusing unit is adapted to induce random scattering despite any adverse external conditions encountered during the surgical procedure. The most likely cause of a potential change in rate of scattering of the laser beam passing through diffusing unit results from contact with tissue. Following a surgical procedure in which the diffusing unit contacts tissue, liquid residue 36, such as sebum, water and cooling gel, as shown in FIG. 6a, may accumulate on diffusively transmitting element 13. The refractive index of liquid residue 36 may be such that, in combination with the refractive index of diffusively transmitting element 13, refracted beam 38 approaches the pattern of collimated beam 24 that impinges on the diffusing unit.

Figure 6B:
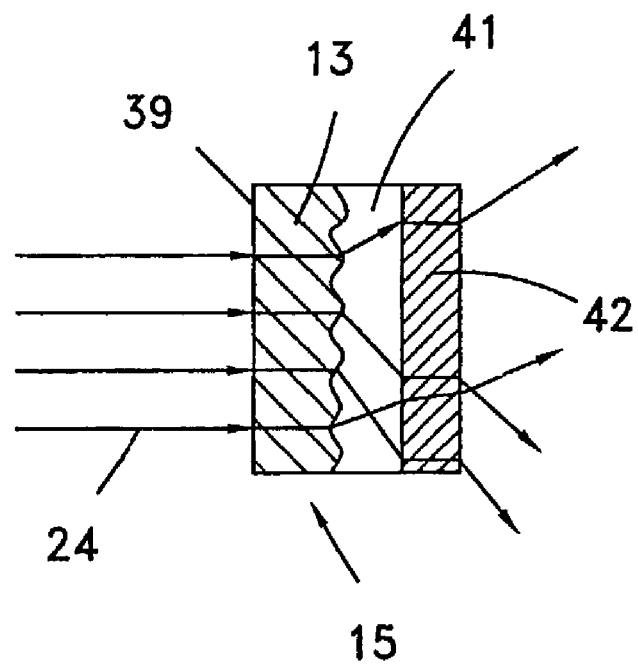
Figure 7A:
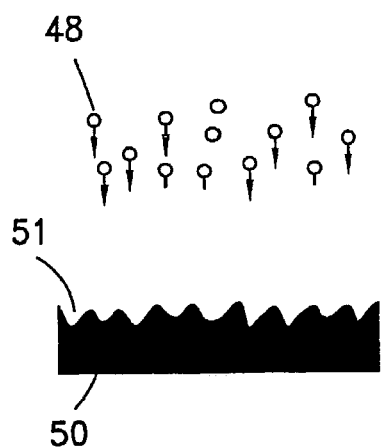
FIG. 7a illustrates the sandblasting of a metallic plate.
Figure 7B:
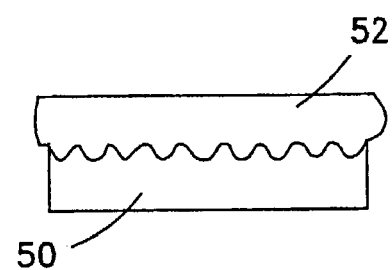
FIG. 7b illustrates the addition of a liquid sensitive to ultraviolet light.
Figure 7D:
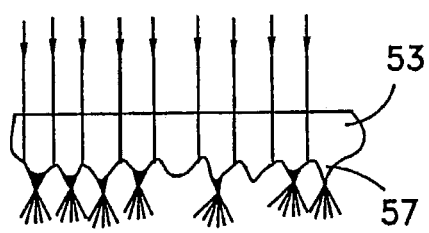
FIG. 7c illustrates the removal of the metallic plate and FIG. 7d illustrates the generation of a scattered laser beam through the microlenses.
Figure 7C:
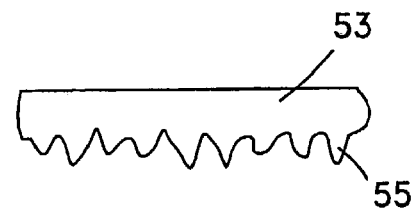

To minimize the risk of injury which may exist if the refracted beam is nearly collimated, diffusively transmitting element 13 is mounted within diffusing unit 15, which is preferably hermetically sealed with sealing element 39 as shown in FIG. 6b, to prevent the accumulation of liquid residue on the former. Clear transmitting element 42 is attached to the distal end of diffusing unit 15 by adhesion and by means of a spacer (not shown), and is separated from diffusively transmitting element 13 by air gap 41. Clear transmitting element 42 and diffusively transmitting element 13 are mutually parallel, and both are perpendicular to the longitudinal axis of diffusing unit 15. When the air gap is less than a predetermined value, a corresponding increase in beam diameter due to scattering is limited, thereby ensuring a minimal effectiveness of the radiation carried by the laser beam for clinical applications. It would be appreciated that accumulation of liquid residue on clear transmitting element 42 will not compromise the inherent safety of a laser unit equipped with a diffusing unit. Since scattering occurs at diffusively transmitting element 13, and the combined index of refraction of air gap 41, clear transmitting element 42 and liquid residue is not sufficient to cause the scattered beam to be once again collimated, the inherent safety of the laser unit is preserved. The accumulation of liquid residue will not affect the clinical efficacy of the laser unit since clear transmitting element 42 is held close to a target during a surgical procedure.

An additional advantage resulting from the separation of clear transmitting element 32 from diffusively transmitting element 13 relates to added safety. Even if clear transmitting element 42 is broken, diffusively transmitting element 13 will scatter the laser beam.

A diffusively transmitting element, adapted to achieve diffusing half angles greater than 45 degrees and as close as possible to an ideal transmitting diffuser, which generates a half angle of 60 degrees, may be produced in several ways:

Sandblasting the surface of a plate of glass, sapphire, acrylic or polycarbonate with fine particles having a size ranging from 1 to 200 microns, depending of the wavelength of the laser beam, comprised of, by example, aluminum oxide;

Sandblasting the surface of a mold plate with fine particles having a size ranging from 1 to 200 microns, depending on the wavelength of the laser beam, comprised of, by example, aluminum oxide and reproducing the contour of the newly formed mold plate surface by pressing hot acrylic, or other suitable material thereon;

Etching the surface of a glass or sapphire plate by chemical means, such as with hydrogen fluoride;

Etching the surface of a glass plate with a scanned focused $CO_2$ laser beam;

Applying a thin sheet of light-diffusing polymer, such as a polycarbonate sheet, a light diffusing acrylic plate, Mylar high quality wax paper or graphical "Pergament Paper" to a glass plate;

Generating a diffraction pattern on the surface of a glass or on a sheet of acrylic or polycarbonate by means of a holographic process to thereby control the divergence angle through the diffraction pattern, which is preferably as large as a half angle of at least 40–45;

Providing a randomly distributed array of thin fibers, arranged e.g. in the form of a conical fiber bundle light concentrator, such as that produced by Schott, Germany, whose aperture is provided with an exit half angle of greater than 40 degrees.

FIG. 7 illustrates the scattering effect that is achieved by sandblasting. As shown in FIG. 7a, metallic plate 50 is bombarded with aluminum oxide particles 48, thereby creating a random distribution of craters 51, each of which having a different size. Liquid 52, which is sensitive to ultraviolet light, is spilled on metallic plate 50 in FIG. 7b and polymerized by ultraviolet radiation. After removal of plate 50, for reuse in the next production batch, transparent frosted plate 53 is produced, as shown in FIG. 7c covered on one side with a random distribution of convex lenses 55 of miniature size. Lenses 55, which have a very short focal length of approximately a few wavelengths, convert a collimated laser beam into a strongly divergent beam with a complete loss of coherence. It is possible to use a similar technique to produce a surface with convex or concave microlenses 57, as shown in FIG. 7d. Microlenses may be produced as well by pressing melted acrylic onto a multi-microlens mold, instead of using a UV curing technique.

Figure 8A:
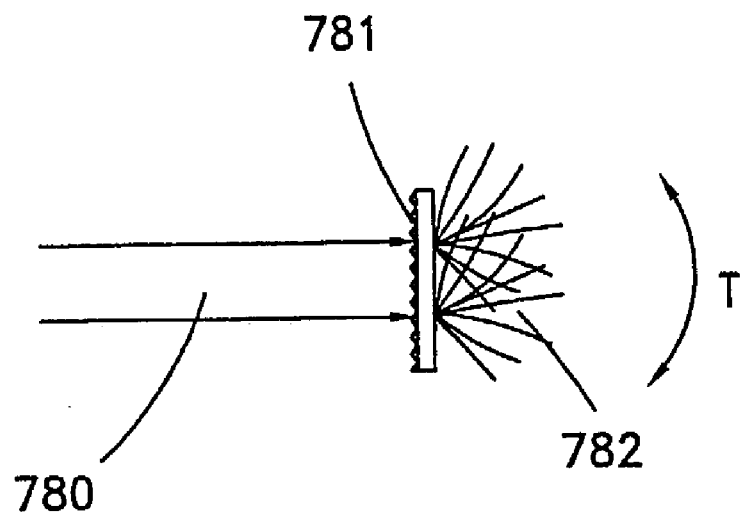
FIG. 8a illustrates one employing a single wide angle diffuser and FIG. 8b illustrates one employing a small angle diffuser.
Figure 8B:
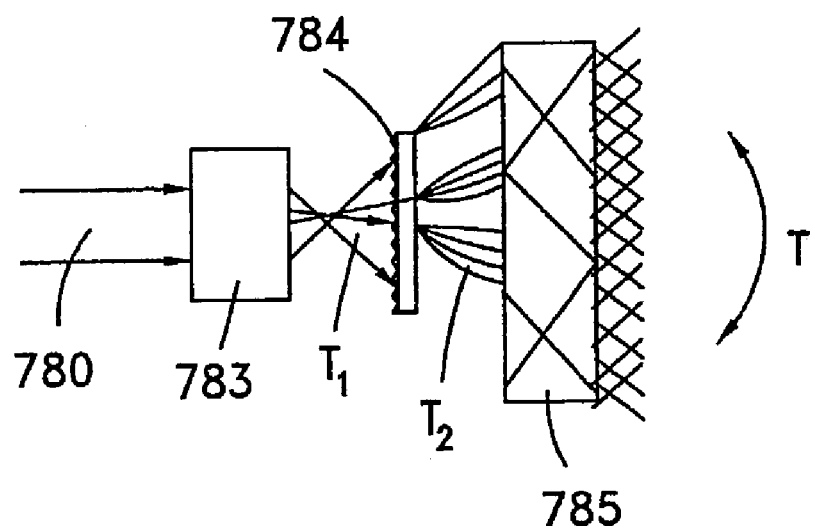

As described above, an exit beam from a laser unit is randomly scattered by a diffusing unit. One type of a diffusing unit is a single wide angle diffuser as shown in FIG. 8a and comprises a diffusively transmitting element 781 which produces scattered light 782 from laser beam 780 having a wide diffusing angle of T. Another type of diffusing unit is shown in FIG. 8b, wherein wide angle diffusion is attained by using divergent optical element 783, and at least one diffuser 784 and refractive/reflective element 785. With this type of diffusing unit, a wide diffusing angle of T is generated in three stages: optical element 783 produces wide angle divergent beam $T_1$ from laser beam 780, diffuser 784 produces a small diffusing angle of $T_2$, and refractive/reflective element 785 expands angle $T_2$ to achieve wide diffusing angle T. Such a multi-component diffusing unit may achieve a wide diffusing angle with the use of elements of high thermal resistance and durability. It will be appreciated that refractive/reflective element 785 may not necessarily be distally disposed with respect to diffuser 784, and may be configured in any other way in order to achieve wide diffusing angle T.

FIG. 9 illustrates another preferred embodiment of a diffusing unit, designated as numeral 200. Diffusing unit 200 is a wide angle diffusing unit, i.e. one that generates a scattering angle that approaches that of an ideal transmitting diffuser, yet is capable of enduring high power laser levels by using glass made of small angle diffusers. Such a diffusing unit is advantageously employed in those applications for which high energy densities are needed for clinical efficacy, and accordingly only a wide-angle scattering angle can ensure eye safety.

As depicted in FIG. 9*a*, optic fiber 201 is disposed adjacent to the proximate end of tapered light guide 202, such that light rays 203 that exit from fiber 201 with half angle divergence A impinge the inner wall of light guide 202. Rays 203 then are reflected from the inner wall of the light guide at an increasingly smaller reflection angle R. The inner wall is coated with a reflective coating so that reflection angle R will be less than the critical angle for total internal reflection. The tapering angle and the dimensions of the light guide as well as the distance of the fiber from the light guide are selected so that exit half angle C of diffused light 208 which propagates from distal end 204 of the light guide is at least 60 degrees. Also, the distance between fiber 201 and distal end 204 is selected so that the energy density of rays 207 emitted from fiber 202 to distal end 204 without any reflection from the light guide wall will be sufficiently low to be considered eye safe when scattered from small angle diffuser 205, e.g. 10 degrees, which induces a relatively small scattering angle and is proximately placed with respect to distal end 204 of the light guide. A small angle diffuser is advantageously selected due the availability of such diffusers, its high durability and capability to withstand a high energy density, as required for aesthetic and industrial applications. Small angle diffuser 205 increases the divergence of difused light 208, in addition to the divergence generated by tapered light guide 202.

In an exemplary diffusing unit, fiber 201 induces a half angle divergence of 25 degrees, the distance from fiber 201 to light guide 202 is 16 mm, the inner diameter of light guide 202 at its proximate end is 15 mm, the tapering angle of light guide 202 is 3 degress, and the length of light guide 202 is 142 mm.

Diffusing unit 200 may also include a second light guide (not shown) which receives diffused light 208 from the distal end of light guide 202. This second light guide is sufficiently long so that diffused light 208, which propagates from small angle diffuser 205, will be emitted from the entire surface of the exit plane of the second light guide. The exit plane of the second light guide therefore functions as an extended diffused source For example, a second light guide having a length of 50 mm and a small angle diffuser which induces a a scattering angle of 10 degrees will enable diffused light to span a diameter of greater than 5 mm at the exit of the second light guide.

As shown in FIG. 9*b*, diffusing unit 200 comprises array of microlenses 210, instead of an optic fiber as in FIG. 8*a*, which is disposed adjacent to the proximate end of tapered light guide 202. Array 210 is configured such that light rays 203 that exit therefrom with half angle divergence A impinge the inner wall of light guide 202.

FIG. 10 illustrates diffusing unit 700, which comprises another type of angular beam expander, namely one which comprises a set of concave and convex mirrors. Small angle fiber 701 from which light rays 703 exit with a small half angle divergence A, such as 5 degrees, is advantageously employed since diffuser unit 700 provides a high angular amplification.

As shown in FIG. 10*a*, half angle divergence A is selected so that a light ray 703 impinges on convex mirror 702 and is reflected therefrom to concave mirror 705. A ray 703 is further reflected from mirror 705 at an angle that enables it to impinge upon, and be scattered by, diffusively transmitting element 710, which is affixed to concave mirror 705. In FIG. 10*b*, diffuser unit 700 is additionally provided with light guide 715. The light which exits from diffusively transmitting element 710 is received by light guide 715 and is reflected within its inner wall, resulting in wide angle diffusing from the entire exit surface of light guide 715. Light guide 715 therefore functions as an ideal extended diffused light source.

Figure 11:
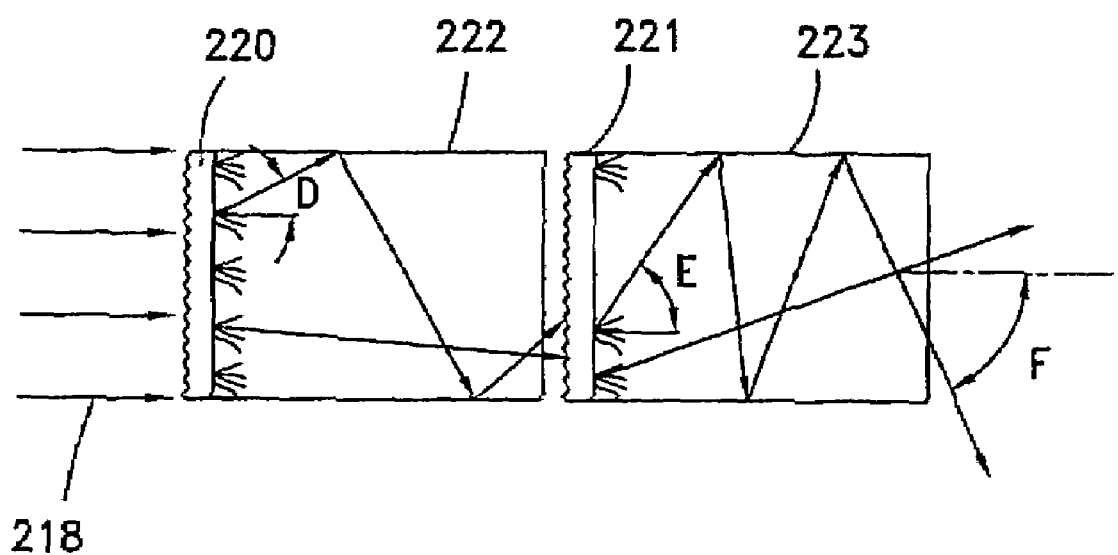
FIG. 11 illustrates a diffusing unit which employs two holographic diffusers, each of which is attached to a corresponding light guide.

FIG. 11 illustrates a diffuser unit in which two 40–45 degrees holographic diffusers 220 and 221 are attached to light guides 222 and 223, respectively. Each holographic diffuser induces a half angle divergence of approximately 45–50 degrees. In order to increase the divergence, two holographic diffusers are used. Light rays 218 propagating from a monochromatic light source are scattered by diffuser 220 to a half angle of D and then are reflected within the inner wall of light guide 222. The scattered light rays are further scattered by diffuser 221 to a half angle of E, are reflected within light guide 223, and exit the diffuser unit at a half angle of F, which approaches 60 degree, the value corresponding to an ideal transmitting diffuser. The light guides are chilled so that the holographic diffusers, which are usually made from plastic material, will also be chilled so that they will be able to withstand the high thermal stress imposed by a high power laser beam. Each light guide may be solid or hollow, and may be made from glass, sapphire, a liquid dielectric, or plastic.

Figure 12B:
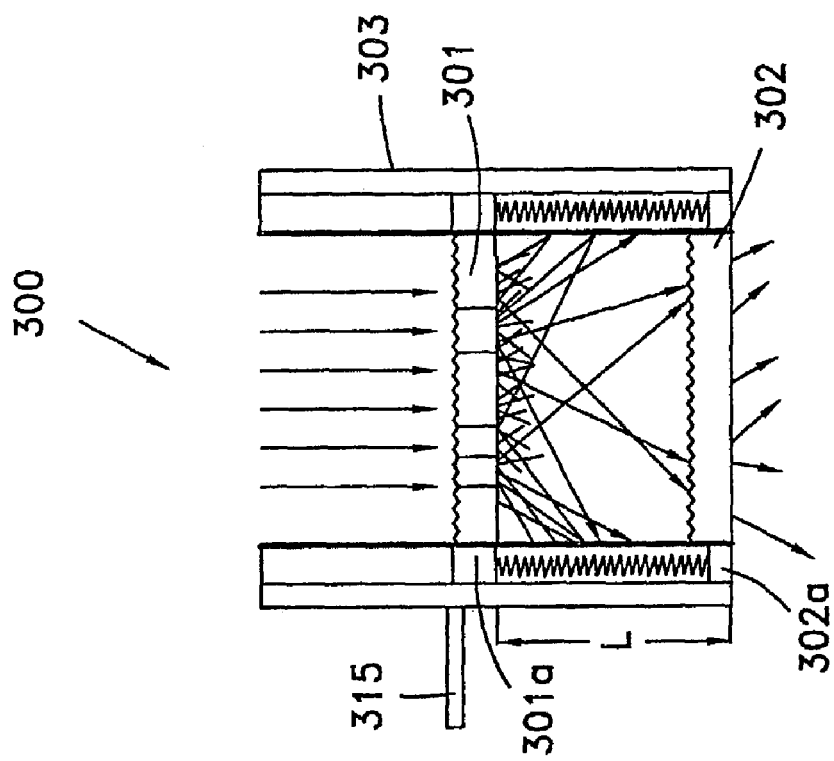
Figure 12A:
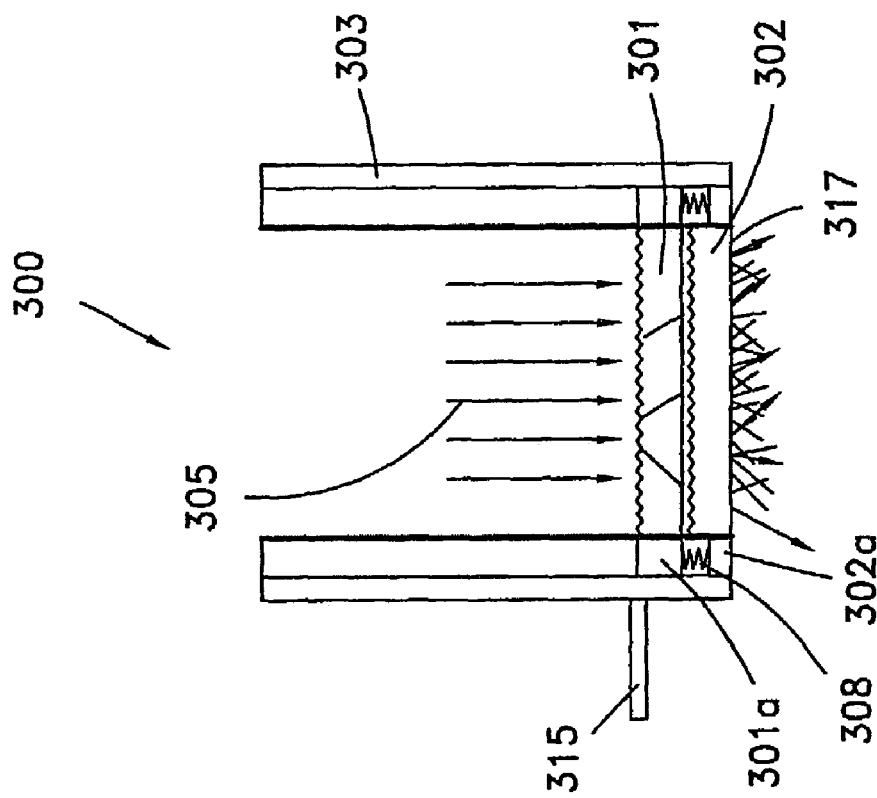
FIG. 12a illustrates the unit in an active position and FIG. 12b in an inactive position.

FIG. 12 illustrates another preferred embodiment of the invention in which diffuser unit 300 comprises two distinct diffusers 301 and 302, wherein at least one is axially displaceable. FIG. 12*a* illustrates diffuser unit 300 in an active position, such that diffusers 301 and 302 are essentially in contact with each other. When in an active position, diffusers 301 and 302 act as a singular randomly scattering diffuser, since substantially all of the monochromatic light 305 that impinges on diffuser 301 is transmitted to diffuser 302. Although the energy density needed for performing an efficacious treatment with monochromatic light 305 is minimally affected, a slight increase of the laser energy can compensate for any energy density losses. FIG. 12*b* illustrates diffuser unit 300 in an inactive position, such that diffusers 301 and 302 are separated from each other by a distance L, which is sufficiently long to ensure that the radiance of the scattered light which exits diffuser 301 and is additionally scattered by diffuser 302 is below a level that is safe to one's eyes.

As shown, diffuser 301 is axially displaceable by means of a plurality of springs 308 that connect diffuser mount 301*a* to diffuser mount 302*a*. When lever 315, which is connected to diffuser mount 301*a*, is depressed springs 308 are compressed and diffuser 301 becomes substantially in contact with diffuser 302, as shown in FIG. 12*a* Distal end 317 of handpiece 303 is then brought in contact with a skin location to be treated by monochromatic light 305 having a high energy density and a high radiance. Upon completion of a desired surgical or cosmetic procedure, lever 315 is released and springs 308 are biased to separate diffuser 301 from diffuser 302 by a distance of L, as shown in FIG. 12*b*, whereby the radiance of the scattered light is below a safe level It will be appreciated that any other means well known to those skilled in the art for axially displacing one or more of the diffusers may be used.

Figure 13:
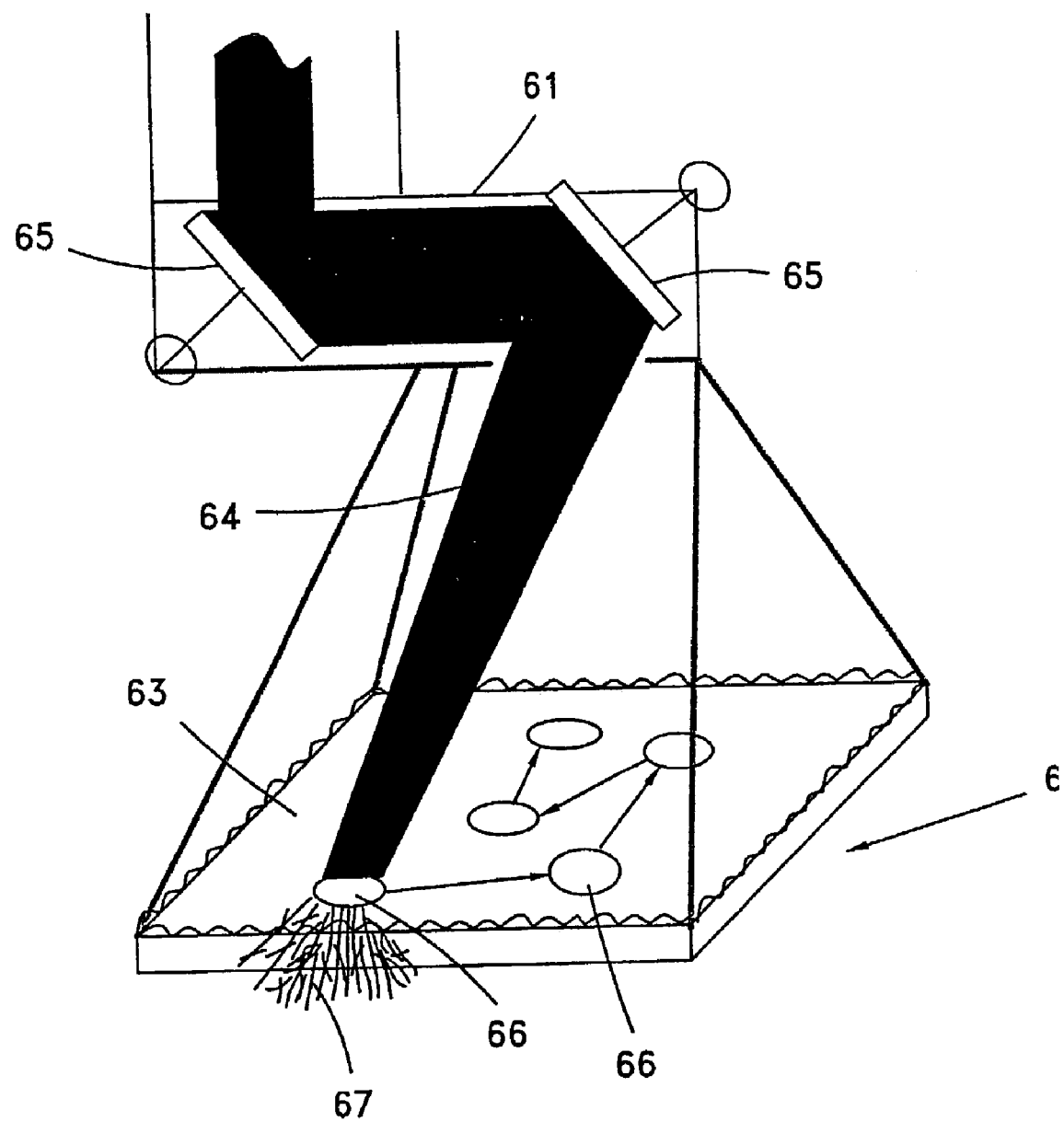
FIG. 13 is a schematic drawing of another preferred embodiment of the present invention in which a scanner rapidly repositions a coherent laser beam onto a plurality of targets on a diffusively transmitting element.

FIG. 13 illustrates an embodiment of the present invention by which tissue, having a larger surface area than the area of the beam impinging thereon, may be treated without overexposure to a laser beam. In prior art systems using a scanner, the treatment beam is quickly displaced in a programmable fashion from one location to another on the tissue to be treated. Although this method provides rapid and reliable treatment, there is a significant risk, however, that the laser beam is liable to be aimed at eyes, skin or flammable materials located in the vicinity of the laser unit.

The diffusing unit generally designated by 60 is shown. In this embodiment the diffusing unit is rigidly attached to delivery system 61, which is provided with a scanner. Diffusively transmitting element 63 is formed with a plurality of visible targets 66 and is placed close to the skin, facing the distal end of delivery system 61. Diffusing unit 60 is preferably provided with a clear transmitting element, as described hereinabove. Coherent collimated or convergent exit beam 64 is directed via a plurality of repositionable reflectors 65 to a predetermined target 66 graphically indicated on diffusively transmitting element 63. The beam that impinges upon a predetermined target 66 is randomly scattered and converted into non-coherent beam 67 whose energy density is essentially similar to that of exit beam 64. Reflectors 65 are controllably repositionable by means of a scanner, whereby they may be displaced from one position and angular disposition to another, so as to accurately direct exit beam 64 to another target 66. The sequence of which target is to receive exit beam 64 after a selected target is programmable and is preferably semi-random to reduce pain which may be felt resulting from the treatment of two adjacent targets, with the time increment between two doses of laser treatment being less that less than a preferred value. A programmable sequence precludes on one hand the chance of a target not to receive an exit beam at all, and on the other hand precludes the chance of not to be inadvertently exposed twice to the exit beam. With the usage of diffusing unit 60, small-diameter beams, e.g. 0.1–7.0 mm, may be advantageously employed to treat a tissue having an area of 16 cm². Similarly, a scanner may be employed for any other feasible wide-area diffusing unit, such as an array of diffusers/light guides incorporating those units illustrated in FIGS. 9–12, whereby an exit laser beam may be directed to each of the diffusers/light guides. Such an array may consist of 9 diffuser/light guides, each having a 3-mm diameter, to cover an area of 81 mm². Scanning may also be achieved by laterally moving an angular expander over the diffuser/light guide array.

FIG. 14 illustrates another preferred embodiment of the invention in which a diffusing unit is not used, but rather a diverging optical element is employed to produce an exit beam having radiance, or alternatively, energy density, depending on the wavelength, below a safe level.

Figure 14A:
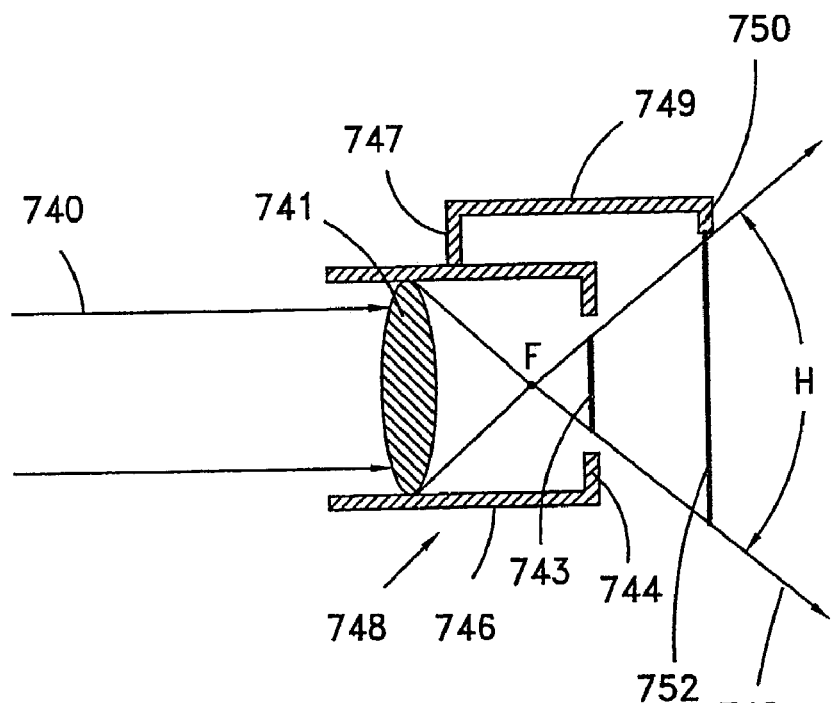
FIG. 14a illustrates a single optical element and FIG. 14b illustrates a plurality of elements.

As shown in FIG. 14a, diverging optical element 741 is placed in diverging unit 748, which is attached to the distal end of the laser unit by any means depicted hereinabove in FIG. 2. Divergent element 741, which is provided with a relatively short focal length, focuses input beam 740 at point F. The beam diverges at a point distally located with respect to point F, as well known to those skilled in the art, and produces divergent beam 742 having a divergent angle of H, a cross section 743 at a plane coplanar with distal end 744 of diverging unit 748 and a cross section 752 at a plane coplanar with shield 750. When divergent beam 742 has a cross sectional dimension at least equal to cross section 752, its radiance is less than an eye safe level.

Pulsed laser radiation in the wavelength range of 1400 nm to 13 microns, according to the ANSI Z 136.1 standard, is considered eye safe if the Accessible Energy Limit (AEL) at the ocular plane is less than a value of $0.56*t^{**}(1/4)$ J/cm², where t is the pulse duration in seconds. For example, a typical pulse duration ranging from 1 to 100 msec is associated with an AEL ranging from 0.1 to 0.3 J/cm², respectively. Accordingly, diverging unit 748 is provided with at least one shield 750, each of which prevents one's head from entering a zone of the divergent beam at which the energy density is greater than the AEL. Shield 750 is connected to tube 746 of diverging unit 748 by means of rigid member 747, and cross member 749. The length of crosss member 749 and the degree of angular divergence H is selected to ensure that the energy density distal to shield 750 is less than the AEL. Normally, cross member 747 is unyielding to head pressure, thereby ensuring eye safety. However, when a lever is actuated, for example, cross member 747 is opened and a spring (not shown), which is normally in a relaxed state and connected to both rigid member 747 and cross member 749, becomes tensed and allows the shield to be proximately displaced. When shield 750 is proximately displaced, distal end 744 of diverging unit 748 may be in contact with a target skin location and cross section 743 of beam 742 having a sufficiently high energy density for a desired application may be utilized. For example, diverging unit 748 is suitable for those applications by which a laser beam is greatly absorbed by water.

Figure 14B:
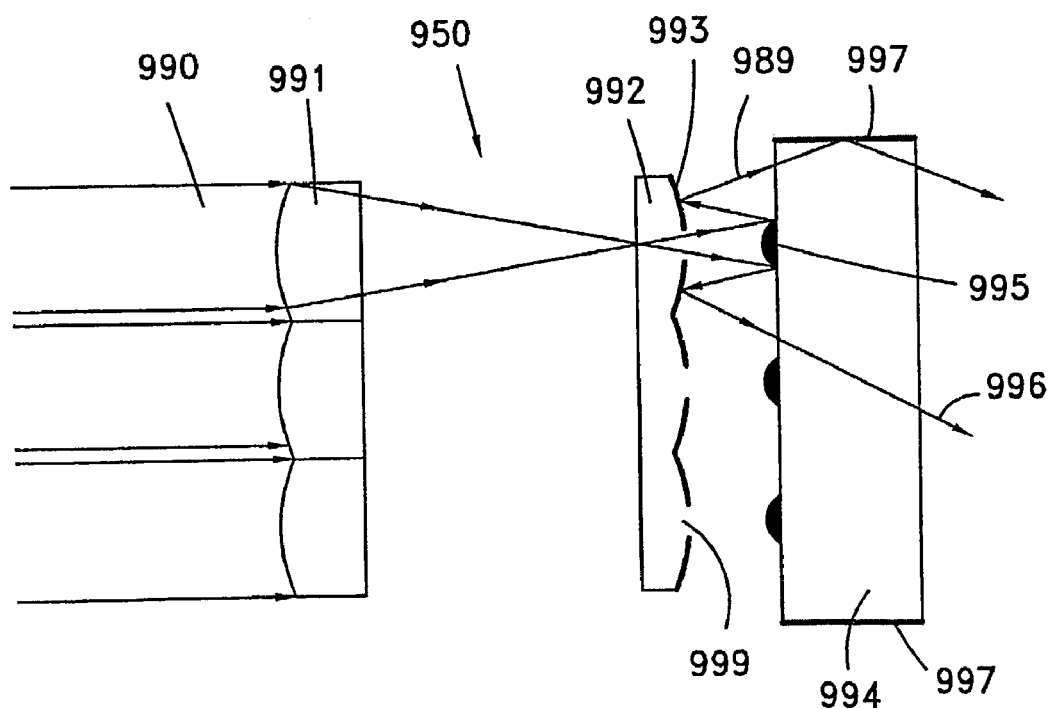

FIG. 14b illustrates diverging unit 950, which comprises array 991 of focusing lenslets each of which has a diameter of e.g. 0.7 mm, array 992 of lenses each of which is provided with reflective coating 993 on its distal side, and a plurality of convex reflectors 995 attached to transparent plate 994. Rays 990 from a collimated laser beam are focused by lenslets 991 and transmitted through non-reflective area 999 formed on the distal side of each lens 992. The location of each non-reflective area 999 is selected so that a focused ray propagating therethrough will impinge upon a corresponding reflector 995 at such a reflecting angle such that it will be reflected therefrom and strike a corresponding reflective coating 993, from which it is again reflected and propagates through transparent plate 994. Most rays, such as ray 996 then exit plate 994. However, some rays, such as ray 989, strike a transversal side 997 of plate 994, which is provided with a reflective coating and causes these rays to exit plate 994. Plate 994 accordingly functions as a light guide when transversally reflecting light rays strike a side 997. The length, i.e. the distance between sides 997, of plate 994 is substantially equal to the length of array 991, and therefore the energy density of an input beam is preserved at the exit of plate 994. In order to comply with the requirements of the aforementioned standards, namely to achieve a safe radiance level with a lens having a diameter of 0.7 mm and producing a divergent half angle of 60 degrees, a lenslet 991 with a focal length of 3 mm may be used to achieve a uniform radiance at a solid angle of approximately steradians.

The distal end of plate 994 may be etched to further diffuse the divergent light exiting therefrom, so that the distal end may function as an extended diffused light source. If desired, the transparent plate may be substituted by a light guide.

In summation, the present invention incorporates four groups of units which cause a monochromatic light to diverge at a sufficiently wide angle so that the radiance of an exit beam is eye safe:

1) A diverging unit provided with a single diverging optical element;
2) A multi-component diverging unit provided with reflective and refractive optical elements, and without any diffusers;
3) A diffusing unit provided with a single thin diffusively transmitting element; and
4) A multi-component diffusing unit, whereby a wide divergent, diffusing angle is achieved by using a high thermally resistant refractive/reflective optical component, as well as at least one thermally resistant low angle diffuser.

When a multi-component diffusing or diverging unit is employed, a relatively simple eye safety monitoring device can be used. Due to the high thermal durability of the selected multi-component unit, the radiance homogeneity is essentially preserved from the proximate end to the distal end thereof. Consequently, limited sampling of the radiance level is required, and an expensive monitoring device is rendered unnecessary Another advantage of a multi-component unit is that monochromatic light reflected from the skin returns to the corresponding unit via a light guide with respect to a diffusing unit and via a transparent plate with respect to a diverging unit, preventing an adverse effect to the skin if reflected monochromatic light were to return thereto.

FIG. 15 illustrates another preferred embodiment of the invention in which a diffusing unit is provided with a skin cooling system. Transparent skin cooling devices are often used in conjunction with skin laser treatments. However they do not scatter laser light and do not reduce the risks associated with exposure to a laser beam. FIGS. 13a–d illustrate prior art skin coolers. In FIGS. 15a and 15b transparent lenses or plates 80 are in contact with tissue 79. Cooling liquid 81, which flows through conduit 83, conducts heat from the heated skin to a cooler. Treatment laser beam 82 propagates without being scattered through the cooling device and penetrates the skin. In FIG. 15c gaseous coolant 84 is used. In FIG. 15d, highly conductive plate 86 is in contact with tissue 79 and chilled by thermoelectric cooler 85.

As shown in FIG. 15e, diffusing unit 75 comprises diffusively transmitting element 74, clear transmitting element 70 and conduit 71 formed therebetween. Conduit 71 is filled with a low temperature gas or liquid of approximately 4° C., which enters conduit 71 through opening 72 and exits at opening 73 The cooling fluid preferably flows through a cooler (not shown). Diffusing unit 75 is positioned in contact with the skin, for treatment and cooling thereof. Clear transmitting element 70 is preferably produced from a material with a high thermal conductivity such as sapphire, in order to maximize cooling of the epidermis. Diffusively transmitting element 74 is disposed such that its proximal face is frosted side and its distal face is planar, facing conduit 71. In FIG. 15f, the diffusing unit comprises diffusively transmitting element 74 made from sapphire, which is chilled at its lateral sides 75 by thermoelectric cooler 76. The proximal side of 74 is frosted and the smooth distal side faces the skin. The parameters of the flowing fluid and of the cooler are similar, by example, to the Cryo 5 skin chiller produced by Zimmer, California, USA. It will be appreciated that any of the skin cooling means illustrated in FIGS. 15d–f may be used to cool skin which is heated as a result of the impingement of monochromatic light thereon even though a diffusively transmitting element is not used.

The eye safety when exposed to the exit beam of a diffusing or diverging unit is significantly improved relative to prior art devices.

Parameters for eye safety analysis are presented in "Laser Safety Handbook," Mallow and Chabot, 1978 in which the standard ANSI Z 136.1 is cited. A laser beam which is reflected from a light diffusing surface is categorized as an extended diffused source if it may be viewed at a direct viewing angle A, greater than a minimum angle Amin, with respect to a direction perpendicular to the source of the laser beam. If a reflected beam may not be viewed at angle A, it is categorized as an intrabeam viewing source. Since a reflected beam is more collimated when viewed at a distance, viewing conditions are intrabeam if the distance R from the source of the laser is greater than a distance Rmax.

Another significant parameter is the maximum permitted radiance, normally referred to as Accessible Energy Limit (AEL) while staring at a diffusing surface which completely reflects a laser beam. AEL depends on the energy density, exposure duration, and wavelength of the laser beam, as well as the solid angle into which the laser beam is diffused. The safety level of a laser unit is evaluated by comparing the AEL to the actual radiace (AR) of the laser beam. Staring at the exit of a diffusing unit according to the present invention is equivalent to staring at a reflecting extended diffuser with 100% reflectivity. The AEL for visible and near infrared radiation exiting a diffusing unit for which protective eyeglasses are unnecessary based on an extended diffuser source is defined by ANSI Z 136.1, as $10*k1*k2*(t^{1/3})$ J/cm²/sr, where t is in seconds and k1=k2=1 for a wavelength of 400–700 nm, k1=1.25 and k2=1 at 750 nm, k1=1.6 and k2=1 at 810 nm, k1=3 and k2=1 at 940 nm and k1=5 and k2=1 at a wavelength of 1060 to 1400 nm. The safety limit set by ISO 15004: 1997 E for pulsed radiation is 14 J/cm²/sr.

The actual radiance (AR) is the actual energy per cm² per steradian emitted from a diffusing unit. The ratio between AEL and AR indicates the safety level of the laser unit employing a diffusing unit, according to the present invention. A ratio less than 1 is essentially unsafe. A ratio between 1.0 and 5 is similar to that of high intensity flashlight sources used in professional photography and intense pulsed light sources used in aesthetic treatments, and is much safer than prior art laser sources. Prior art laser sources which do not incorporate a diffusing unit have a ratio which is several orders of magnitudes less than 1.

Table I below presents a comparison in terms of eye safety between the exit beam of monochromatic light after being scattered by a diffusing unit into a solid angle of 3.14 sr, which is equivalent to that attained by an ideal transmitting diffuser, according to the present invention. The parameters for a non-coherent diode-based laser unit are based on one produced by Dornier Germany. The parameters for a non-coherent Alexandrite-based laser unit are based on one produced by Sharplan/ESC (Epitouch). The parameters for a non-coherent Nd:YAG-based laser unit intended for hair removal are based on one produced by Altus, USA. The parameters for a noncoherent Nd:YAG-based laser unit intended for photo-rejuvenation are based on one produced by Cooltouch, USA. The parameters for a non-coherent dye-based laser unit are based on one produced by ICN (Nlight). The parameters for an intense pulsed light laser unit are based on one produced by ESC. The AEL for a particular wavelength and pulse duration is based on the aforementioned ANSI Z 136.1 standard.

TABLE I

| System type | Non coherent Diode based | Non coherent Alexandrite based | Non coherent Nd:YAG based | Non coherent Nd:YAG based | Non coherent Dye based | Intense Pulsed Light | CW Diode 60 degrees diffuser |
|---|---|---|---|---|---|---|---|
| Application | Hair removal | Hair removal | Hair removal | Photo-rejuvenation | Photo-rejuvenation | Hair removal | Tooth whitening |
| Parameters | | | | | | | |
| Wavelength | 940 nm | 755 nm | 1064 nm | 1320 nm | 585 nm | 645–900 nm | 980 nm |
| Energy | 6 J | 10 J | 11.3 J | 7 J | 0.6 J | 90 J | 1.5 J |
| Pulse duration | 50 msec | 40 msec | 60 msec | 60 msec | 0.5 msec | 40 msec | 1 sec |
| Spot size | 5 mm | 7 mm | 6 mm | 6 mm | 5 mm | 10 × 30 mm$^2$ | 5 × 5 mm$^2$ |
| Energy density | 30 J/cm$^2$ | 25 J/cm$^2$ | 40 J/cm$^2$ | 25 J/cm$^2$ | 3 J/cm$^2$ | 30 J/cm$^2$ | 6 J/cm$^2$ |
| Extended view parameters | | | | | | | |
| A min | 8 mrad | 3.5 mrad | 4 mrad | 4 mrad | 2.5 mrad | 5 mrad | 15 mrad |
| R max | 0.4 m | 2 m | 2 m | 2 m | 1.3 m | 4 m | 0.33 m |
| Eye safety Parameters | | | | | | | |
| AEL/sr | 11 J/cm$^2$/sr | 4.3 J/cm$^2$/sr | 19.5 J/cm$^2$/sr | 20 J/cm$^2$/sr | 0.79 J/cm$^2$/sr | 3.4 J/cm$^2$/sr | 35 J/cm$^2$/sr |
| AR/sr | 9.6 J/cm$^2$/sr | 8 J/cm$^2$/sr | 12.7 J/cm$^2$/sr | 8 J/cm$^2$/sr | 0.79 J/cm$^2$/sr | 9.5 J/cm$^2$/sr | 8 J/cm$^2$/sr |
| Eye safety | | | | | | | |
| Figure of merit AEL/AR | 1.14 | 0.53 | 1.54 | 2.5 | 1 | 0.35 | 4.1 |

The table shows that the exit beam according to the present invention is essentially as eye-safe, or safer than, broad band non-coherent intense pulsed light sources, such as those used for professional photography or those used for cosmetic surgery. The scattered monochromatic light, for most of the light sources, does not necessitate protective eyeglasses and is safer than an accidental glance into the sun for a fraction of a second. Although the ratio for the Alexandrite and Intense Pulsed Light sources is less than 1 and protective eyeglasses must be worn, the required optical attenuation for these light sources is less than 3, much less than the required optical attenuation with the use of a conventional monochromatic light source not provided with a diffusing unit, which is on the order of $10^4$–$10^7$. It will be appreciated that a similar level of eye safety for laser units utilizing a diffusing unit may be achieved with a very wide scattering angle, approaching a half angle of 60 degrees or a solid angle of steradians. Small angle scattering may result in a different level of eye safety when operated at an energy density suitable for aesthetic treatments; nevertheless, such a scattered exit beam is much safer than the exit beam of a conventional coherent laser unit.

Figure 16:
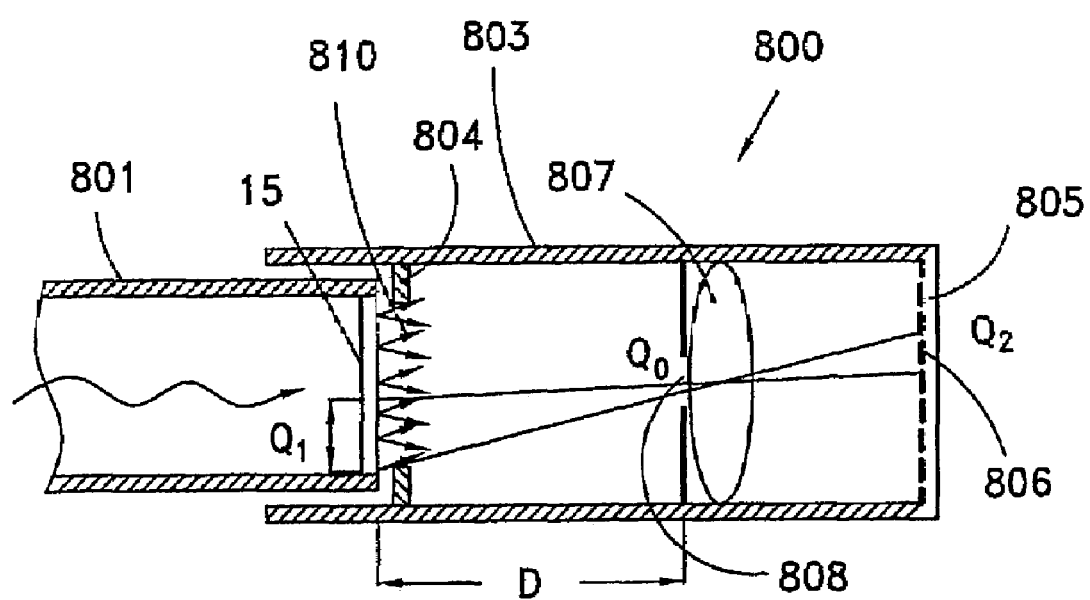
FIG. 16 illustrates an eye safety measurement device.

The radiance of the light emitted by a diffusing unit can be measured to verify that it is in compliance with the appropriate standards for laser eye safety. In one embodiment, a converted laser utilizing a diffusing unit in accordance with the present invention is provided with an eye safety measurement device. Such a device may be an energy meter such as that produced by Ophir, USA or an array of light detectors 805 as depicted in FIG. 16. The eye safety measurement device is provided with control circuitry which is in communication with the operating system of the laser unit, so that, as a result of a mishap, a warning is issued indicating that protective eyeglasses are required if the measured radiance of a scattered laser beam is greater than a predetermined safe value. Alternatively, the control circuitry may discontinue operation of the laser unit if the measured radiance of a scattered laser beam is greater than a predetermined safe value.

FIG. 16 illustrates an exemplary eye safety measurement device, designated as numeral 800. Device 800 is operative to measure the radiance of scattered light 810, which is scattered by means of diffusing unit 15 attached to distal end 809 of laser unit handpiece 801. Device 800 is provided with an array of light detectors 806, e.g. complementary metal oxide semiconductor (CMOS) detectors which provide light imaging, at distal end 805 thereof, on which scattered light 810 impinges after passing through aperture 808 of diameter $Q_o$ and lens 807. After distal end 809 is inserted into a complementary opening formed within device 800 until contacting annular abutment plate 804 perpendicular to outer wall 803 of device 800, the laser unit is fired. For purposes of clarity, light which propagates the rough segment $Q_1$ of diffusing unit impinges on segment $Q_2$ of detector array 806. The radiance of scattered light 810 therefore is determined by dividing the amount of energy sensed by detectors 806 by diameter $Q_0$ of aperture 808 and by the solid angle characteristic of the detector structure. For example, the distance D between abutment plate 804 and aperture 808 is 200 mm, segment $Q_1$ of the diffusing element 15 is 0.7 mm, and diameter $Q_0$ of the aperture is 7 mm, to comply with the regulations set forth in ANSI Z 136.1.

FIG. 17 illustrates another embodiment of the invention, wherein eye safety in the vicinity of a laser unit that emits an infrared beam or other invisible radiation is increased by adding a flashing device to the laser system to cause one's eyes to blink during the propagation of the laser beam.

Figure 17A:
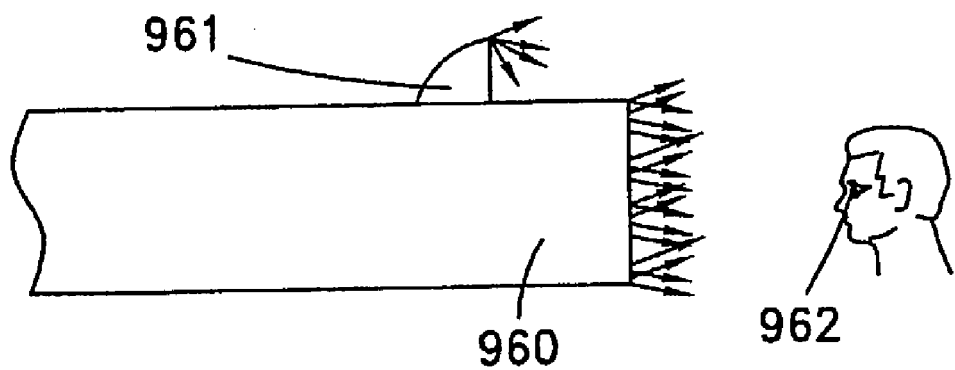
FIG. 17a illustrates one that induces uncontrolled blinking before firing a laser beam.

FIG. 17a illustrates distal end 960 of a laser unit, which emits light 955 generated therefrom, preferably being scattered monochromatic light when a diffusing unit is employed. To prevent damage to eye 962 of a bystander located in the vicinity of the laser unit, flashing device 961 is added to distal end 960. Flashing device 961 generates a short visible light flash a fraction of a second prior to the firing of a laser beam.

Figure 17B:
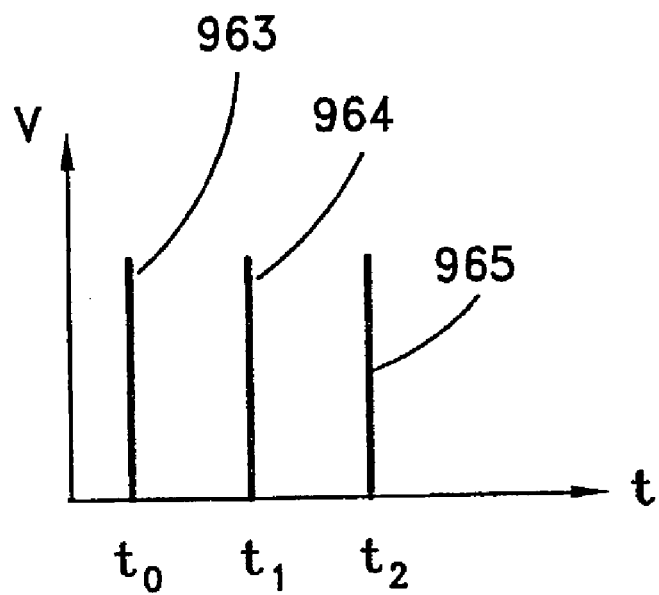
FIG. 17b is a timing diagram corresponding to the flashing device of FIG. 17a, and 17c illustrates a flashing device that detects a retroreflected beam from an eye within firing range of a laser beam.

As shown in FIG. 17b, activation of the laser unit initiates an electrical pulse 963 at time $t_0$, which triggers a timer circuit (not shown). The timing circuit is adapted to generate and transmit pulse 964 at time $t_1$ to flashing device 961, to produce a flash is sensed by eye 962. Flashing device 961 may be a well known flashing means associated with cameras or may utilize diodes, or any other feasible means to produce an instantaneous flash. After a predetermined period of time, the timing circuit transmits a pulse to the control system of the laser unit to fire a laser beam at time $t_2$. This predetermined period of time, namely the difference between $t_2$ and $t_1$, is approximately 0.25 seconds, equal to the reaction time of uncontrolled blinking as a response to light, and is preferably no more than 0.20 seconds. A flashing device 961 may be added to any source of monochromatic light, such as any type of laser or IPL sources, whether producing visible or invisible light.

Figure 17C:
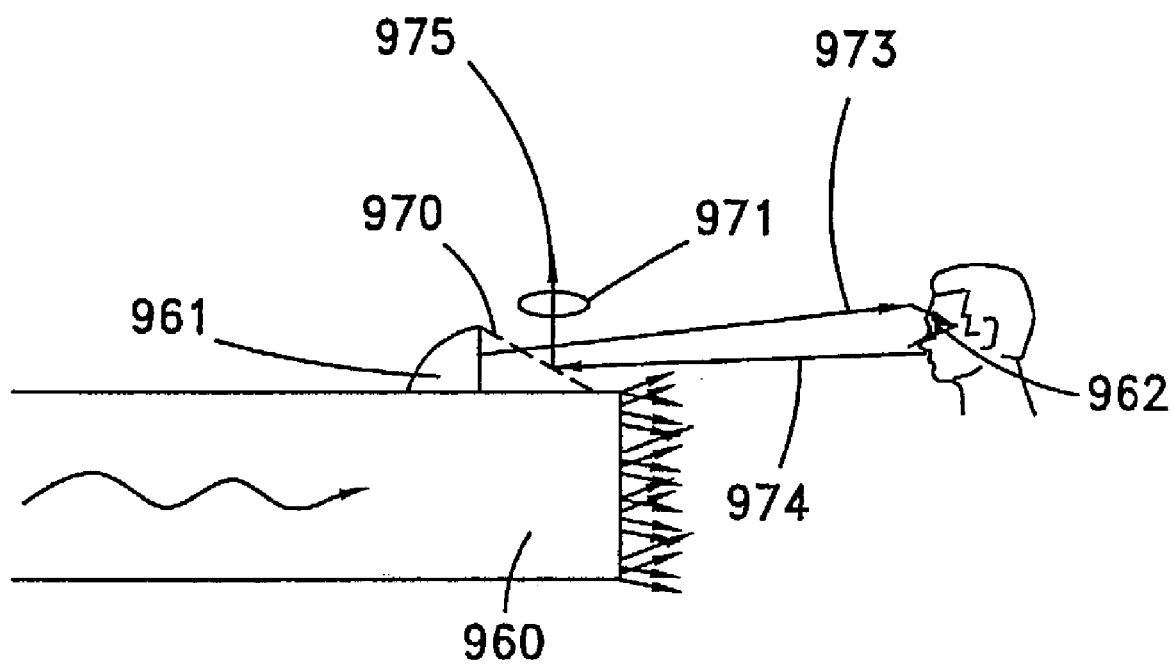

FIG. 17c illustrates another application of flashing device 961. By generating a flash with device 961 and determining whether detector 975 senses light retroreflected from eye 962, a microprocessor (not shown) in communication with a control circuit (not shown) and with detector 975, e.g. a photodetector, can determine that eye 962 is in danger of being injured from the imminent firing of a laser beam from the laser unit. The choroid layer of the retina diffusely reflects light source 973 that impinges thereon from the previously generated flash, and the optics of eye 962 re-image, or retroreflect, the light back to flashing device 961. Retroreflected beam 974 is reflected from beam splitter 970 through a lens (not shown) onto 975. Two additional adjacent detectors (not shown) detect light reflected from other areas in the room in which the laser unit is disposed. If the signal generated by detector 975 has a much larger amplitude than the signals generated by the additional detectors, the microprocessor determines that eye 962 is in firing range of a laser beam. The control circuit of flashing device 961 then sends a disabling signal to the control system of the laser unit to thereby prevent firing of a laser unit. When detector 975 is used to detect a retroflected beam, and a flash is generated within the predetermined time before the firing of a laser beam, as illustrated in FIG. 17b, in order to cause uncontrollable blinking of the eye during propagation of the beam, the laser unit is inherently fail-safe. That is to say, even if the eye does not blink, detector 975 will determine that eye 962 is in firing range of a laser beam and the laser unit will cease operation.

As can be seen from the above description, a diffusing/diverging unit of the present invention, which is mounted to the exit aperture of a conventional laser unit, induces the exit beam to be divergent/and or scattered at a wide angle. As a result the exit beam is not injurious to the eyes and skin of observers, as well as to objects located in the vicinity of the target. Nevertheless, the exit beam generally retains a similar level of energy density as the beam generated from the exit aperture when the diffusing unit is very close or essentially in contact with the target, and is therefore capable of performing various types of treatment, both for cosmetic surgery and for industrial applications. Protective eyeglasses are generally not needed, and if they are needed, conventional sunglasses would be the only requirement, thereby allowing work in an aesthetic clinic to be less cumbersome.

EXAMPLE 1

An experiment was performed to demonstrate the operating principles of the present invention in which transparent light diffusing adhesive "Magic Tape," manufactured by 3M, having a thickness of 100 microns was attached to the distal end of an Alexandrite laser unit having a diameter of 8 mm. The energy level of the laser beam is 11 J/pulse. The laser beam was directed to the white (rear) side of a black developed photographic paper having a thickness of 300 microns. For comparison, the laser beam was also directed to the photographic paper without the use of the adhesive tape.

The ablation of the black paper after the beam had propagated and scattered through the white paper provides a visual simulation of the capability of the laser beam to penetrate transparent light-scattering skin in order to treat black hair follicles (or any other type of lesion) under the skin.

The energy of the laser beam transmitted through the adhesive tape, which caused the laser beam to scatter, was measured by directing the beam to an energy meter located at a distance of 1 mm from the distal end of the laser unit. The energy of the scattered laser beam dropped from 11 to 10 J. The results of this experiment indicate that the diffusively transmitting element did not absorb a significant amount of energy, since a loss of 10% is expected in any case due to Fresnel reflection.

When the laser beam was directed to the white (rear) side of a developed photographic plate at a distance of 1 mm, an ablation of the black color on the opposite side of the photographic paper resulted. There was no difference in the results between usage of light diffusing tape or not. This experiment demonstrates that the performance of a non-coherent Alexandrite laser beam, according to the present invention, at a distance of 1 mm is essentially equal to the corresponding coherent laser beam.

When the laser beam was directed, without the addition of light diffusing tape, at the photographic paper from a distance of at least 8 mm, an ablation resulted that is identical to that which was generated from a short distance of 1 mm. However, when light diffusing tape was applied to the exit aperture of the laser unit from a distance of at least 8 mm, the scattered beam did not result in an ablation. Accordingly, the present invention allows for a high level of safety and lack of damage to bodily tissue when disposed at a relatively large distance therefrom.

EXAMPLE 2

In a second experiment a long pulse Alexandrite laser unit having a wavelength of 755 nm, pulse duration of 40 msec, and having an energy density of 25 J/cm$^2$ was used for hair removal. A diffusing unit with an ultra-densely woven polymer-based diffuser having a half angle of 15 degree produced by Barkan or a holographic diffuser produced by Physical Optics Corporation (USA) having a half angle of 40 degrees was employed. The diffusers were used in a one-time basis. Chilling gel was applied between the diffuser and the skin.

Each pulse of a laser beam scattered by a diffusing unit formed a spot of 5.5 mm on various skin locations including arms, bikini lines and armpits of 10 patients Full hair removal was noticeable immediately after the firing of the laser beam. Each spot was compared to a control area with an identical diameter formed by an unscattered laser beam generated by the same laser unit with similar parameters, and similar results were achieved. Hair did not return to those spots for a period of one month.

EXAMPLE 3

A long pulse Alexandrite laser unit having a wavelength of 755 nm, pulse duration of 40 msec, and having an energy level of 1–20 J is suitable for hair removal.

The diameter of the diffusing unit is 7 mm, and its scattering half angle is 60 degrees. A diffusing unit comprising a diffuser with a small scattering angle, a highly divergent lens and a light guide is added to the distal end of the laser unit.

The prior art energy density of 10–50 J/cm$^2$ is not significantly reduced with the employment of a diffusing unit. The laser unit operates at 25 J/cm$^2$ and generates a radiance of 8 J/cm$^2$/sr. Since the acceptable radiance limit according to ANSI Z 136.1 is 4.3 J/cm$^2$/sr, bystanders are required to use protective eyeglasses with 50% optical attenuation, an attenuation similar to that of sunglasses and an order of 100,000 less than typical protective eyeglasses worn during operation of a laser unit. For a larger target area, a scanner such as the Epitouch model manufactured by Lumenis may be used.

A diffusing unit having a diameter of up to 7 mm is particularly suitable for lower energy lasers, which are relatively small, remove hair at a slower speed from limited area and are inexpensive. An application of such a laser, when employed with a diffusing unit, includes the removal of eyebrows.

EXAMPLE 4

A pulsed Nd:YAG laser unit such as one produced by Altus (USA) or Deka (Italy) having a wavelength of 1064 nm, pulse duration of 100 msec, and having an energy level of 0.5–60 J is suitable for hair removal at an energy density ranging from 35–60 J/cm$^2$.

A diverging unit with an array of focusing lenslets, an array of lenses provided with reflective coating on its distal side, and a plurality of convex reflectors attached to a transparent plate is used, such that the diverging half angle is close to 60 degrees. When a laser beam having an energy density of 40 J/cm$^2$ is generated, a radiance of 12.7 J/cm$^2$/sr at the exit of the diverging unit is induced, approximately half of the maximal permitted radiance according to ANSI Z 136.1.

EXAMPLE 5

A long pulse diode laser unit having a wavelength ranging from 810–830 nm, or of 910 nm or 940 nm pulse duration ranging from 1–200 msec, and having an energy level of 0.5–30 J is suitable for hair removal at an energy density ranging from 20–50 J/cm$^2$.

The diameter of the treated area, or spot size, ranges from 1–20 mm. The diffusively transmitting element is preferably made from fused silica, sapphire, or is a holographic diffuser used in conjunction with a light guide or with any other diffusing unit described hereinabove. The scattering half angle is close to 60 degrees. A scanner may be integrated with the diffusing unit. The delivery system to which the diffusing unit is attached may be a conical light guide, such as that manufactured by Coherent or Lumenis, a guide tube produced e.g. by Diomed or a scanner produced e.g. by Assa. With a diffusing unit having a diameter of 5 mm and a laser beam generated with an energy density of 20 J/cm$^2$ and a pulse duration of 100 msec, the radiance at the exit of the diffusing unit is 9.6 J/cm$^2$/sr, lower than the maximal permitted radiance value of 11.0 J/cm$^2$/sr.

EXAMPLE 6

A miniature diode laser unit for home use operating at a wavelength of approximately 810 nm, or 940 nm, such as one produced by Dornier, Germany, and having a power level of 4 W is suitable for hair removal. The invention converts a continuous working diode laser unit, which is in a high safety class and usually limits operation to the medical staff, into a lower safety class, similar to non-coherent lamps of the same power level.

The diffusing unit utilizes an angular beam expander with a convex reflector, a concave reflector having an inner diameter of 16 mm, a 10-degree glass diffuser, and a light guide having a length of 20 mm and an inner diameter of 2 mm. The diameter of the treated area, or spot size, is approximately 2 mm. The energy density at the exit of the light guide is 30 J/cm$^2$ and the radiance thereat is approximately 10 J/cm$^2$/sr. A scanner may be integrated with the diffusing unit. The diode laser may also be used without a scanner, in which case the laser will be pulsed for a duration of approximately 300 msec.

EXAMPLE 7

A Ruby laser unit having a wavelength of 694 nm, pulse duration ranging from 0.5–30 msec, and having an energy level of 0.2–20 J is suitable for hair removal.

The diameter of the treated area, or spot size, ranges from 1–20 mm. The larger spot sizes can be generated by Ruby lasers manufactured by Palomar, ESC and Carl Basel, which provide an energy density ranging from 10–50 J/cm$^2$. The smaller spot sizes can be generated by inexpensive low energy lasers, which are suitable for non-medical personnel. A multi-component diffusing or diverging unit may be used. The laser unit is much safer than a conventional laser unit A scanner, such as manufactured by Assa of Denmark or by ESC, may be used to displace a reflected collimated beam from one aperture to another formed within the diffusing or diverging unit. The scanning rate is variable, and the dwelling time at each location ranges from 20–300 msec.

EXAMPLE 8

High risk laser units, such as Nd:YAG having a wavelength of 1.32 microns and manufactured by Cooltouch with a pulse duration of up to 40 msec, a dye laser having a wavelength of 585 nm and manufactured by N-Light/SLS/ICN, or a Nd:Glass laser having a wavelength of 1.55 microns with a pulse duration of 30 millisec may be used for non-ablative skin rejuvenation. This application is aimed at the treatment of rosacea, mild pigmented lesions, reduction of pore sizes in facial skin and mild improvement of fine wrinkles, without affecting the epidermis. The advantage of these lasers for non-ablative skin rejuvenation is related to the short learning curve and more predicted results due to the small number of treatment parameters associated with the single wavelength. By implementing a diffusing unit, the laser unit becomes safe and may be operated by non-medical personnel.

An N-Light laser unit is initially operated at an energy density of 2.5 J/cm$^2$ for collagen contraction. The addition of a diffusing unit makes the laser unit as safe as an IPL. The addition of a multi-component diffusing or diverging unit with a divergent half angle of 60 degrees and an exit diameter of 5 mm results in a radiance level of 0.79 J/cm$^2$/sr, which is equal to maximal accepted limit.

A laser beam may be generated with a considerably less expensive laser unit, having an energy level ranging from 0.5–3 J and a slow repetition rate such as 1 pps, and generating a spot size ranging from 2–4 mm. In the case of wrinkle removal, the operator may follow the shape of the wrinkles with a small beam size. Such a non-coherent laser beam having a beam size of 2–4 mm is particularly suitable for aestheticians. Using a diffusing unit depicted in FIG. 10*b* with a 10 degree diffuser and a light guide having a length of 30 mm results in a laser unit with a radiance of approximately 0.5 $J/cm^2/sr$.

EXAMPLE 9

A pulsed Nd:YAG laser unit having a wavelength of 1064 nm and manufactured by ESC and having an energy level of 0.5–60 J is suitable for treatment of vascular lesions. The pulse duration ranges from 1–200 msec, depending on the size of the vessels to be coagulated (300 microns to 2 mm) and the depth thereof below the surface of the skin. A LICAF (Litium Calcium Fluoride) laser unit at a wavelength of 940 nm may also be advantageously used for this application, and its associated laser beam is better absorbed by blood than the Nd:YAG or Dye laser. A Dye laser at a wavelength of 585 nm and manufactured by Candela may be used to treat vessels located at a low depth below the skin surface, such as those observed in port wine stain, telangectasia and spider veins.

The diameter of the treated area, or spot size, ranges from 1–10 mm, depending on the energy level. A multi-component diffusing or diverging unit is used, due to the relatively high energy density of greater than 90 $J/Cm^2$ needed for the treatment of deep vascular lesions A scanner may be integrated with the diffusing unit.

EXAMPLE 10

Q-Switch laser units having a pulse duration ranging from 10–100 nsec and having an energy density of 0.2–10 $J/cm^2$ is suitable for removal of pigmented spots, mostly on the face and hands, as well as removal of a tattoos. A Q-switched Ruby laser as manufactured by ESC or Spectrum, a Q-Switch Alexandrite laser manufactured by Combio, and a Q-Switch Nd:YAG laser may be used for such an application.

The diameter of the treated area, or spot size, ranges from 1–10 mm, depending on the energy level. A diffusing unit utilizing two diffusively transmitting elements is used, wherein one is fixed while the other is axially displaceable such that both elements are essentially in contact with each other in an active position, e.g. a gap of approximately 0.2 mm when a laser beam is fired. The gap between the two elements is approximately 15 cm when the laser is not fired. The diameter of the diffusing unit is 6 mm. Each diffusively transmitting element is preferably made from glass, sapphire or polymer.

The addition of such a diffusing unit with an axially displaceable diffuser to the aforementioned laser units is instrumental in rendering pigmented lesion and tattoo removal to be a considerably less risky procedure. Tattoo removal is achieved only by means of a laser beam, and is not attainable with intense pulse light sources.

The removal of pigmented lesions may also be performed with the use of an Erbium laser unit operated at a wavelength of 3 microns. Most pigmentation originates from the epidermis, and such a laser beam penetrates only a few microns into the skin. With implementation of a diffusing unit, this procedure may not necessarily be performed by medical specialists Aestheticians will be able to treat a large number of patients, particularly since an Erbium laser is relatively inexpensive.

Another application of the present invention involves the field of dentistry, and relates to the treatment of pigmented lesions found on the gums. Q-switched as well as Erbium lasers may be used for this application.

EXAMPLE 11

A $CO_2$ laser may be used for wrinkle removal. In prior art devices, such a laser is used in two ways in order to remove wrinkles: by ablation of a thin layer of tissue at an energy density greater than 5 $J/cm^2$ with a Coherent Ultrapulse, ESC Silktouch, or Nidek $CO_2$ laser and scanner for a duration less than 1 msec; or by non-ablative heating of collagen in the skin for lower energy densities, such as at 3 W, which may be achieved by operation of a continuously working ESC derma-K laser for 50 msec on a spot having a diameter of 3 mm.

With implementation of the present invention in which a multi-component diffusing or diverging unit is attached to a $CO_2$ laser, a laser beam having a wavelength of 10.6 microns may be generated. As opposed to other far infrared sources whose thermal and spectrally broad bandwidth involves less control of penetration depth, the interaction of a laser beam with tissue according to the present invention is highly controllable and its duration can be very short.

The diffusing and diverging units are preferably made from a lenslet that is transparent to a $CO_2$ laser beam such as ZnSe or NaCL. The diameter of the diffusing unit ranges from 1–10 mm. The divergent angle is greater than the minimal acceptable value so as to produce a radiance level at the exit beam that is essentially eye safe.

During ablation, a clear transmitting element of the diffusing unit is separated from the tissue to be treated by a thin spacer having a thickness of approximately 1 mm to allow for the evacuation of vapors or smoke produced during the vaporization process.

Similarly an Erbium laser unit operating at an energy density above 2 $J/cm^2$ and generating a laser beam greater than 3 microns may be used for wrinkle removal. Ablation is shallower than attained with a $CO_2$ laser and application of an Erbium laser unit can be extended to tatto or permanent make up removal.

EXAMPLE 12

A Nd:YAG or oyher laser unit may be used for treatment of herpes. A diode laser with selective absorption of Cyanin green or other materials by fatty lesions may be used for treatment of acne. Both of these lasers may be used for treatment of hemorrhoids and for podiatric lesions on the feet.

EXAMPLE 13

A dye laser unit operating at a wavelength of approximately 630 nm or 585 nm, or at other wavelengths which are absorbed by natural porpherins present in P acne bacterias, such as produced by Cynachore or SLS, as well as a laser unit operating at 1.45 microns as produced by Candella, may treat acne lesions. The addition of a diffusing or diverging unit to the laser unit may considerably enhance eye safety and simplify the use of the laser unit for such treatments by nurses and non-medical staff.

EXAMPLE 14

$CO_2$, diode and Nd:YAG laser units operating at an average power of approximately 1–10 W are currently used by physicians to treat pain. The addition of a diffusing unit may enable the use of a highly safe device for that procedure in pain clinics by non-medical personnel. Each laser unit may generate a number of repetitively occurring sets of pulses, during a period of approximately 3 seconds. The delivery system of the laser beam may be an articulated arm or an optical fiber

EXAMPLE 15

A diode laser unit manufactured by Candella (USA) generating a laser beam with an energy density of 10 $J/cm^2$, a wavelength of 1445 nm, a pulse duration of 100 msec and a spot size of 3 mm is suitable for non-ablative photorejuvenation.

A diverging unit with a single converging lens focuses the beam to a focal zone 1.5 mm proximate to the distal end of the diverging unit and and produces a half angle divergence of 45 degrees. The diverging unit is provided with a shield located 10 mm distal to the focal point, whereat the energy density is reduced to an eye safe level of 0.2 $J/cm^2$ and a spot size is 23 mm.

EXAMPLE 16

It is advantageous to use an eye-safe laser unit for welding. The employment of a diffusing unit is an excellent way to reduce the risks associated with laser welding.

When welding thin transparent parts, such as those made from plastic, e.g with a diode laser unit, it is often advantageous to employ a large surface scanner or a large diameter beam which will irradiate a large surface area and selectively activate all targets with appropriate chromophores (by heat). Such a scanner is in contrast to a scanner which is specifically targeted to the geometrical locations at which welding materials are present. The dwelling time of the welding laser beam at the targets depends on the size of the welding element and the depth of material to be melted. The dwelling time is also dependent on the size of a target treated in photothermolysis. As an example, welding a strip having a thickness of 50 micron to a substrate necessitates a dwelling time of approximately 1 msec, while a strip having a thickness of 200 microns requires a dwelling time of 16 msec. The dwelling time is proportional to the square of the thickness. Some welding chromophores are transparent in the visible part of the spectrum, but exhibit strong absorption in the near infrared part of the spectrum.

EXAMPLE 17

Another industrial application for the present invention is associated with microstructures to be evaporated. Paint stains or ink may be selectively evaporated from surfaces such as clothes, paper and other materials that need cleaning by use of various pulsed lasers. One example of this application is related to the restoration of valued antiques. Another example is the selective vaporization of metallic conductors which are coated on materials such as glass, ceramics or plastics. Vaporization of metallic conductors can be achieved with a pulsed laser, which is generally separated by a short distance from a target and whose beam has a duration ranging from 10 nanoseconds to 10 milliseconds. Pulsed Nd:YAG lasers are the most commonly used ablative industrial lasers, although other lasers are in use as well. Pulsed Nd:YAG industrial lasers may attain an energy level of 20 J concentrated on a spot of 1 mm, equivalent to an energy density of 2000 $J/cm^2$, The addition of a diffusing unit to an industrial laser considerably increases the safety of the ablative device.

Pulsed Nd:YAG laser units are also suitable for improving the external appearance of larger structures, such as the cleaning of buildings, stones, antique sculptures and pottery. The laser units in use today are extremely powerful, having a continuously working power level of up to 1 kW, and are therefore extremely risky. The addition of a diffusing unit considerably improves the safety of these laser units.

A diffusing unit, when attached to an Excimer laser unit, is suitable for photo-lithography, or for other applications which use an Excimer laser unit for a short target distance.

With the addition of a multi-component diffusing or diverging unit, all of these applications become much safer to a user.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

The invention claimed is:

1. Method of performing an aesthetic or medical treatment which is bodily safe to bystanders exposed to a monochromatic treatment light source, comprising the steps of:
    a) providing an eye-hazardous monochromatic treatment light source;
    b) attaching a diffusing unit to the distal end of said light source, said diffusing unit including at least one diffusively transmitting element which is transparent to said light and constitutes an extended diffused source when exposed to said light;
    c) positioning said distal end at a predetermined location substantially in contact with an outer surface of a target, said location being suitable for effecting an aesthetic or medical treatment;
    d) firing said monochromatic treatment light;
    e) causing said monochromatic light to scatter at said distal end such that the radiance of the light exiting said distal end is an eye safe level; and
    f) allowing said scattered light to propagate to said target so as to effect an aesthetic or medical treatment,
    whereby at a first position of said distal end relative to said target corresponding to said predetermined location the energy density of an exit beam from said distal end is suitable to effect said treatment and at a second position of the distal end relative to, and above, said target the energy density of the scattered light emitted from said distal end is significantly less than the energy density which is suitable to effect said treatment.

2. Method of claim 1, wherein the radiance of the scattered monochromatic light is less than $10*k1*k2*(t^{1/3})$ $J/cm^2/sr$, where t is a laser pulse duration in seconds, k1=k2=1 for a wavelength ranging from 400 to 700 nm, k1=1.25 and k2=1 for a wavelength of approximately 750 nm, k1=1.6 and k2=1 for a wavelength of approximately 810 nm, k1=3 and k2=1 for a wavelength of approximately 940 nm, and k1=5 and k2=1 for a wavelength ranging from 1060 to 1400 nm.

3. Method of claim 2, wherein the monochromatic light source is selected from the group consisting of Excimer, Dye, Nd:YAG 1064, 1320 and 1440 nm, frequency doubled Nd:YAG laser, Ruby laser, Alexandrite laser, Diode lasers operating at a wavelength of 810 to 830 nm, 940 nm, and 1450 nm, stack of diode laser, LICAF laser, Er:Glass laser, Er:YAG laser, Er:YSGG laser, $CO_2$ laser, isotopic $CO_2$ laser and Holmium laser.

4. Method of claim 3, wherein the aesthetic or medical treatment is effected when the monochromatic light source is housed in a handpiece.

5. Method of claim 2, wherein the monochromatic light is provided with a wavelength ranging from 308 to 1600 nm or between 1750 nm to 11.5 microns.

6. Method of claim 3 wherein the monochromatic light source is a plurality of monochromatic diodes.

7. Method of claim 1, further comprising measuring the radiance of the scattered monochromatic treatment light and issuing a warning as a result of a mishap if the radiance of the scattered monochromatic light is greater than a predetermined safe value.

8. Method of claim 1, wherein the eye hazardous monochromatic light is selected from the group consisting of collimated laser beam, convergent laser beam, concentrated multiple laser beams and fiber guided laser beam.

9. Method of claim 1, wherein the bodily safety includes eye safety, skin safety and environmental safety.

10. Method of claim 1, wherein the aesthetic or medical treatment is selected from the group consisting of hair removal, coagulation of blood vessels located on a face or legs, treatment of rosacea, tattoo removal, removal of pigmented lesions in the skin, skin rejuvenation, treatment of psoriasis, treatment of acne, treatment of skin piamented with porphyrins or Cyanine green, treatment of fat, skin resurfacing, skin vaporization, collagen contraction, dental applications, removal of pigments from the gums, teeth whitening, dermatology, gynecology, podiatry, urology, and reduction of pain.

11. Method of claim 1, wherein a laser beam exiting a diffusively transmitting element is controllably repositionable to scan targets.

12. Method of claim 11, wherein the sequence of targets to be impinged by the laser beam is programmable.

13. Method of claim 1, wherein the monochromatic light is pulsed with a pulse duration ranging from 10 nanosecond to 1500 msec, the energy density level of the monochromatic light source ranges from 2 to 90 $J/cm^2$, and the diffusing unit has a diameter of greater than 3 mm.

14. Method of claim 13, wherein a series of pulses is generated.

15. Method of claim 1, further comprising the step of cooling a skin target during generation of the treatment light.

16. Method of claim 15, comprising the steps of:
a) providing a diffusing unit comprising a diffusively transmitting element and a clear transmitting element proximal to said diffusively transmitting element, the diffusively transmitting element and clear transmitting elements being transparent to the monochromatic light and being mutually parallel and perpendicular to the longitudinal axis of the diffusing unit;,
b) positioning said clear transmitting element at a predetermined location above an outer surface of a target which is suitable for effecting the treatment;
c) providing means for skin cooling, said skin cooling means being disposed in a gap formed between the diffusively transmitting and clear transmitting elements or in contact with one of the diffusively transmitting element and the clear transmitting element;
d) firing the monochromatic treatment light; and
e) allowing said skin cooling means to cool said target.

17. Method of claim 16, wherein the gap formed between the diffusively transmitting and clear transmitting elements is less than 2 mm.

18. Method of claim 16, wherein the skin cooling means is a fluid transparent to the monochromatic light and flowable through a conduit inserted within the gap.

19. Method of claim 18, wherein the fluid is in fluid communication with an external cooler.

20. Method of claim 16, wherein the skin cooling means is a thermoelectric cooler, said thermoelectric cooler operative to cool lateral sides of the clear transmitting element which is positioned at a predetermined location substantially in contact with an outer surface of the skin target.

21. Method of claim 1, further comprising the steps of:
a) positioning a U-shaped evacuation chamber between the diffusing unit and the target such that its lateral ends are in contact with the target;
b) evacuating vapors from said evacuation chamber through a gap formed by its central open region; and
c) firing the monochromatic treatment light source.

22. Method of claim 21, further comprising the step of moistening the outer surface of a skin target with water or gel prior to the step of firing the monochromatic light source.

23. Method of improving bodily safety of bystanders exposed to a monochromatic light source, comprising:
a) providing a monochromatic light source with a distal end;
b) providing a diffusing unit with a plurality of diffusers at said distal end, wherein at least one of said diffusers is axially displaceable;
c) axially displacing said at least one axially displaceable diffuser to an active position such that each diffuser is substantially in contact one with the other, whereby the energy density of an exit beam from said diffusing unit is substantially equal to the energy density of the monochromatic light at the first position of the distal end of the monochromatic light source; and
d) axially displacing said at least one axially displaceable diffuser to an inactive position such that each diffuser is separated one from the other by a gap large enough to generate a sufficiently large scattering angle such that the energy density of the light emitted from said diffusing unit at the second position of the distal end of the monochromatic light source is significantly less than the energy density of the monochromatic light.

24. Method of claim 23, wherein the first position is substantially in contact with a target to which the monochromatic light is directed.

25. Method for converting an eye-hazardous laser unit suitable for aesthetic treatment or medical treatment into an eye safe laser unit, comprising the steps of:
a) providing a diffusing unit comprising at least one planar diffusively transmitting element longer than 3 mm which is transparent to light emitted by an eye-hazardous laser unit suitable for aesthetic treatment or medical treatment;
b) attaching said diffusing unit to the distal end of said laser unit;
c) firing said laser unit; and
d) allowing said light to propagate through said diffusing unit, thereby generating a non-coherent and extended diffused source of light from said unit at a sufficiently low radiance value such that said source of light is eye safe to bystanders exposed to said light and of a sufficiently high energy density level at said distal end to effect said aesthetic treatment or medical treatment when said distal end is essentially in contact with a target.

26. Aesthetic or medical treatment apparatus which is bodily safe to bystanders exposed to a monochromatic light source, comprising: means attached to the distal end of an eye hazardous monochromatic treatment light source, said means adapted to cause the monochromatic light to be divergent, whereby at a first position of said distal end corresponding to a predetermined location substantially in contact with an outer surface of a target the energy density of an exit beam from said distal end is suitable for effecting an aesthetic or medical treatment and at a second position of said distal end relative to, and above, said target the energy density of the light emitted from said distal end is significantly less than the energy density of the monochromatic light which is suitable for effecting said treatment, wherein the radiance of the divergent monochromatic light is less than $10*k1*k2*(t^{1/3})$ J/cm$^2$/sr, where t is a laser pulse duration in seconds, $k1=k2=1$ for a wavelength ranging from 400 to 700 nm, $k1=1.25$ and $k2=1$ for a wavelength of approximately 750 nm, $k1=1.6$ and $k2=1$ for a wavelength of approximately 810 nm, $k1=3$ and $k2=1$ for a wavelength of approximately 940 nm, and $k1=5$ and $k2=1$ for a wavelenath ranging from 1060 to 1400 nm.

27. Apparatus of claim 26, wherein the diverging means comprises a diverging unit provided with at least one focusing lens, a plurality of reflectors and a distally positioned plate transparent to the monochromatic light, each of said at least one lens provided with a suitable focal length so as to focus the monochromatic light onto at least one of said reflectors, each of said reflectors positioned so as to allow light rays to exit said plate at varying angles, depending on the number of times reflected by said plurality of reflectors, whereby to cause said monochromatic light to be divergent.

28. Apparatus of claim 26, wherein the diverging means is also a scattering means.

29. Apparatus of claim 28, wherein the scattering means comprises a diffusing unit attachable to the distal end of the monochromatic light source, said diffusing unit including at least one diffusively transmitting element that is transparent to essentially coherent monochromatic light.

30. Apparatus of claim 29, wherein the material of each diffusively transmitting element is selected from the group consisting of silica, glass, sapphire, diamond, non-absorbing polymer, light diffusing polymer, polycarbonate, acrylic, densely packed fibers, NaCl, CaF$_2$, glass, ZnSe and BaF$_2$.

31. Apparatus of claim 29, wherein each diffusively transmitting element is provided with a plurality of irregularities which are randomly distributed thereabout.

32. Apparatus of claim 29, wherein the diffusively transmitting element is formed by a diffraction pattern or by a randomly distributed array of thin fibers.

33. Apparatus of claim 29, wherein a half angle of a scattered exit beam exceeds 42 degrees.

34. Apparatus of claim 29, further comprising a scanner for rapid repositioning of the monochromatic light to a target on the diffusively transmitting element.

35. Apparatus of claim 29, further comprising a plurality of reflectors, the angular disposition and distance of each reflector relative to the diffusing unit being repositionable, whereby to accurately direct the monochromatic light to a selected target on the diffusively transmitting element.

36. Apparatus of claim 35, further comprising a processor, said processor suitable for the programming of the sequence of targets to be impinged by the monochromatic light.

37. Apparatus of claim 28, wherein the scattering means comprises a diffusing unit attachable to the distal end of the monochromatic light source, said diffusing unit including an angular beam expander and at least one diffuser.

38. Apparatus of claim 37, wherein the diffusing unit further comprises at least one light guide, each of said light guides being provided with internally reflecting walls and an exit surface.

39. Apparatus of claim 38, wherein a light guide is tapered.

40. Apparatus of claim 38, wherein a light guide is made of a material selected from the group consisting of solid glass, sapphire, plastic and liquid dielectric material.

41. Apparatus of claim 38, further comprising an optical element which increases the divergence angle of monochromatic light and a diffuser which receives light from said optical element and emits said received light to the light guide, the exit surface of said light guide functioning as a wide angle extended diffuser source.

42. Apparatus of claim 26, wherein a divergent angle of the divergent monochromatic light is greater than a half angle of 6 degrees.

43. Apparatus of claim 26, further comprising a means for measuring the radiance of the divergent monochromatic light, control circuitry in communication with said measuring means and the monochromatic light source, and a warning means in communication with said control circuitry which is activated, as a result of a mishap, if the radiance of the divergent monochromatic light is greater than a predetermined safe value.

44. Apparatus of claim 26, wherein the monochromatic light source is one or more arrays of a diode light source.

45. Apparatus of claim 26, wherein the first position is substantially in contact with a target to which the monochromatic light is directed.

46. Apparatus of claim 26, wherein the eye hazardous monochromatic light is selected from the group consisting of collimated, laser beam, convergent laser beam, concentrated multiple laser beams and fiber guided laser beam.

47. Apparatus of claim 26, wherein the monochromatic light is provided with a wavelength ranging from 308 to 1600 nm or between 1750 nm to 11.5 microns and the energy density level of the monochromatic light source ranges from 2 to 90 J/cm$^2$.

48. Apparatus of claim 26, wherein the monochromatic light source is a plurality of monochromatic diodes.

49. Apparatus of claim 26, wherein the bodily safety includes eye safety, skin safety and environmental safety.

50. Apparatus of claim 26, wherein the monochromatic light source is selected from the group consisting of Excimer laser, Dye laser, Nd:YAG 1064, 1320 and 1440 nm laser, frequency doubled Nd:YAG laser, Ruby laser, Alexandrite laser, Diode laser including diodes operating at a wavelength of 810 to 830 nm, 940 nm, and 1450 nm, stack of diodes, LICAF laser, Er:Glass laser, Er:YAG laser, Er:YSGG laser, CO$_2$ laser, isotopic CO$_2$ laser and Holmium laser.

51. Apparatus of claim 50, wherein the light source is housed in a handpiece.

52. Apparatus of claim 50, wherein the duration of a laser pulse ranges from 10 nanoseconds to 1500 msec, the energy density level of the monochromatic light source ranges from 2 to 90 J/cm$^2$, and the diverging means has a width of greater than 3 mm.

53. Apparatus of claim 26, wherein the aesthetic or medical treatment is selected from the group consisting of hair removal, coagulation of blood vessels located on a face or legs, treatment of rosacea, tattoo removal, removal of pigmented lesions in the skin, skin rejuvenation, treatment of psoriasis, treatment of acne, treatment of skin pigmented with porphyrins or Canine green, treatment of fat, skin resurfacing, skin vaporization, collagen contraction, dental applications, removal of pigments from the gums, teeth whitening, dermatology, gynecology, podiatry, urology, and reduction of pain.

54. Apparatus of claim 26, wherein the distance between a distal end of the diverging means and the target at the first position of the distal end of the monochromatic light source is the smaller of 2 mm and the diameter of the monochromatic light.

55. Apparatus of any of claim 26, wherein a unit is attached to the distal end of the monochromatic light source by an attachment means.

56. Apparatus of claim 55, wherein the unit is fixedly attached to the distal end of the monochromatic light source.

57. Apparatus of claim 55, wherein the unit is integrally formed together with the distal end of the monochromatic light source during manufacturing, the unit being disposed internally to the outer wall of the monochromatic light source.

58. Apparatus of claim 55, wherein the attachment means is releasable.

59. Apparatus of claim 58, wherein the attachment means is permanently attached to the monochromatic light source and displaceable, whereby in one position of a displaceable unit the monochromatic light source is coherent, not propagating through said displaceable unit, and in a second position at which said displaceable unit is attached to the distal end of the monochromatic light source, the monochromatic light is noncoherent, propagating through the displaceable unit.

60. Apparatus for improving bodily safety of bystanders exposed to a monochromatic light source, comprising a diffusing unit attachable to a monochromatic light source distal end, said diffusing unit comprising a plurality of diffusers wherein at least one of said diffusers is axially displaceable, such that at an active position the plurality of diffusers are substantially in contact one with the other at a the first position of said distal end relative to a target at which the energy density of an exit beam from said distal end is substantially equal to the energy density of the monochromatic light, and at an inactive position each of said diffusers is separated one from the other by a gap such that the energy density of the light emitted from the diffusing unit at a second position of said distal end relative to a target is significantly less than the energy density of the monochromatic light.

61. Apparatus for improving bodily safety of bystanders exposed to a monochromatic light source, comprising scattering means attached to the distal end of an eye hazardous monochromatic light source, whereby at a first position of said distal end relative to, and substantially in contact with, a target the energy density of an exit beam from said scattering means is substantially equal to the energy density of the eye hazardous monochromatic light and at a second position of said distal end relative to a taraet the energy density of the light emitted from said scattering means is significantly less than the energy density of the eye hazardous monochromatic light, wherein the scattering means comprises a diffusing unit attachable to the distal end of the eye hazardous monochromatic light source, said diffusing unit comprising at least one diffusively transmitting element that is transparent to essentially coherent monochromatic light and a clear transmitting element proximal to a diffusively transmitting element, the diffusively transmitting element and clear transmitting elements being mutually parallel and perpendicular to the longitudinal axis of the diffusing unit, wherein a gap between the diffusively transmitting and clear transmitting elements is less than 2 mm.

62. Apparatus of claim 61, further comprising means for skin cooling, said skin cooling means being disposed in the gap formed between the diffusively transmitting and clear transmitting elements or in contact with one of the diffusively transmitting element and the clear transmitting element, said skin cooling means adapted to reduce the rate of increase of temperature at a target skin location.

63. Apparatius of claim 62, wherein the skin cooling means is a fluid transparent to the monochromatic light and flowable through a conduit inserted within the gap.

64. Apparatus of claim 63, wherein the fluid is in fluid communication with an external cooler.

65. Apparatus of claim 63, wherein the fluid is a liquid or a gas.

66. Apparatus of claim 62, wherein the skin cooling means is a thermoelectric cooler, said thermoelectric cooler operative to cool lateral sides of a clear transmitting element which is positioned at a predetermined location substantially in contact with an outer surface of the skin target.

67. Apparatus of claim 62, further comprising a scanner for rapid repositioning of the monochromatic light to a target on the diffusively transmitting element, the skin cooling means capable of continuously cooling the skin at a corresponding skin location.

68. Apparatus of claim 61, wherein the clear transmitting element is made of a material selected from the group of glass, sapphire, transparent polymer including polycarbonate and acrylic, $BaF_2$, NaCi and $ZnF_2$.

69. Apparatus for improving bodily safety of bystanders exposed to an eye hazardous monochromatic light source, comprising means attached to the distal end of a monochromatic light source which is adapted to cause the monochromatic light to be divergent, whereby at a first position of said distal end relative to, and substantially in contact with, a target the energy density of an exit beam from said diverging means is substantially equal to the energy density of the eye hazardous monochromatic light and at a second position of said distal end relative to a target the energy density of the light emitted from said diverging means is significantly less than the energy density of the eye hazardous monochromatic light, and means to evacuate vapors or particles from said target.

70. Apparatus of claim 69, wherein the evacuation means is U-shaped in vertical cross-transmission element, to allow for contact with a target at its lateral ends and for evacuation of vapors through a gap formed by its central open region.

71. Apparatus of claim 70, wherein the target of the exit beam from the distal end is a skin target and the monochromatic light is pulsed light having a wavelength ranging from 308 to 1600 nm, an energy density ranging from 0.1 to 200 $J/cm^2$ which is suitable for the non-ablative treatment of skin lesions located under the outer surface of said skin target, and a pulse duration ranging from 10 nanoseconds to 1500 msec.

72. Apparatus of claim 71, wherein the energy density level of the monochromatic light is adjustable to a level which is sufficient for the temporal spectral absorption of a subcutaneous skin target and the pulse duration of the monochromatic light is adjustable in accordance with the color or skin type of the skin target, the monochromatic light source being selected from the group of Excimer laser, Dye laser, Nd:YAG 1064, 1320 and 1440 nm laser, frequency doubled Nd:YAG laser, Ruby laser, Alexandrite laser, Diode laser operating at a wavelength of 810 to 830 nm, 940 nm, and 1450 nm, stack of diodes, LICAF, and an intense pulsed light source.

73. Apparatus of claim 72, wherein the monochromatic light is suitable for effecting a treatment selected from the group of hair removal, skin rejuvenation, collagen contraction, treatment of acne, treatment of skin pigmented with porphyrins or Cyanine green, treatment of herpes, and removal of pigmented lesions in the skin.

74. Apparatus of claim 72, wherein the light source and evacuation means are housed in a common handpiece.

75. Apparatus of claim 74, wherein the evacuation means is releasably attachable to the handpiece.

76. Apparatus of claim 70, further comprising skin cooling means, said skin cooling means adapted to reduce the rate of increase of temperature at a target skin location.

77. Apparatus according to claim 69, wherein the diverging means is also a scattering means, said scattering means comprising a diffusing unit attachable to the distal end of the monochromatic light source, said diffusing unit including at least one diffusively transmitting element that is transparent to essentially coherent monochromatic light.

78. Apparatus of claim 77, wherein the diffusing unit further comprises a clear transmitting element proximal to a diffusively transmitting element, the diffusively transmitting element and clear transmitting elements being mutually parallel and perpendicular to the longitudinal axis of the diffusing unit, a gap between the diffusively transmitting and clear transmitting elements being less than 20 mm.

79. Apparatus of claim 78, wherein the gap is less than 2 mm.

80. Apparatus according to claim 69, wherein the evacuation means is interposed between the diverging means and the target.

81. Apparatus of claim 69, wherein the diverging means is provided with at least one focusing lens, a plurality of reflectors and a distally positioned plate transparent to the monochromatic light, each of said at least one lens provided with a suitable focal length so as to focus the monochromatic light onto at least one of said reflectors, each of said reflectors positioned so as to allow light rays to exit said plate at varying angles, depending on the number of times reflected by said plurality of reflectors, whereby to cause said monochromatic light to be divergent.

82. Apparatus for improving bodily safety of bystanders exposed to a monochromatic light source, comprising:

a) means attached to the distal end of an eye hazardous monochromatic light source, said means adapted to cause the monochromatic light to be divergent, whereby at a first position of said distal end relative to, and substantially in contact with, a target the energy density of an exit beam from said diverging means is substantially equal to the energy density of the eye hazardous monochromatic light and at a second position of said distal end relative to a target the energy density of the light emitted from said diverging means is significantly less than the energy density of the eye hazardous monochromatic light, b) means for generating a visible flash; and c) control circuitry in communication with said means for generating a visible flash and with the monochromatic light source, said control circuitry synchronized such that a flash is generated prior to the emission of each pulse of monochromatic light.

\* \* \* \* \*

UNITED STATES PATENT AND TRADEMARK OFFICE
CERTIFICATE OF CORRECTION

| | |
|---|---|
| PATENT NO. | : 7,184,614 B2 |
| APPLICATION NO. | : 10/614672 |
| DATED | : February 27, 2007 |
| INVENTOR(S) | : Slatkine |

It is certified that error appears in the above-identified patent and that said Letters Patent is hereby corrected as shown below:

On Title page item 30
Add the following on the front page of the patent:

Claim of Foreign Priority:
Israel 147009 filed on December 10, 2001
Israel 150094, filed on June 6, 2002
International application PCT/IL01/00855, filed on August 2, 2002

Signed and Sealed this

First Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,184,614 B2
APPLICATION NO. : 10/614672
DATED : February 27, 2007
INVENTOR(S) : Slatkine Page 1 of 1

It is certified that error appears in the above-identified patent and that said Letters Patent is hereby corrected as shown below:

On Title page item 30
Add the following on the front page of the patent:

Claim of Foreign Priority:
Israel 147009, filed on December 10, 2001
Israel 150094, filed on June 6, 2002
International application PCT/IL02/00635, filed on August 2, 2002.

Signed and Sealed this

Fourteenth Day of October, 2008

JON W. DUDAS
*Director of the United States Patent and Trademark Office*